US009567550B2

(12) United States Patent
Ueda et al.

(10) Patent No.: US 9,567,550 B2
(45) Date of Patent: Feb. 14, 2017

(54) FRAGRANCE COMPOSITION

(71) Applicant: Kao Corporation, Tokyo (JP)

(72) Inventors: Junko Ueda, Wakayama (JP);
Yoshiharu Ataka, Wakayama (JP);
Takahiro Asada, Wakayama (JP);
Naotoshi Toki, Kanagawa (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/404,694

(22) PCT Filed: May 30, 2013

(86) PCT No.: PCT/JP2013/065058
§ 371 (c)(1),
(2) Date: Dec. 1, 2014

(87) PCT Pub. No.: WO2013/180224
PCT Pub. Date: Dec. 5, 2013

(65) Prior Publication Data
US 2015/0118174 A1    Apr. 30, 2015

(30) Foreign Application Priority Data
Jun. 1, 2012    (JP) ................. 2012-126075

(51) Int. Cl.
| | | |
|---|---|---|
| *C11B 9/00* | (2006.01) | |
| *A61K 8/34* | (2006.01) | |
| *C07C 29/143* | (2006.01) | |
| *C11D 3/50* | (2006.01) | |
| *A61Q 19/10* | (2006.01) | |
| *A61Q 15/00* | (2006.01) | |
| *A61Q 13/00* | (2006.01) | |
| *C07C 31/125* | (2006.01) | |
| *A61Q 5/02* | (2006.01) | |
| *D06M 13/00* | (2006.01) | |
| *C07C 29/145* | (2006.01) | |
| *D06M 13/144* | (2006.01) | |
| *C07C 45/66* | (2006.01) | |
| *C07C 45/72* | (2006.01) | |

(52) U.S. Cl.
CPC ............. *C11B 9/0015* (2013.01); *A61K 8/34* (2013.01); *A61K 8/342* (2013.01); *A61Q 5/02* (2013.01); *A61Q 13/00* (2013.01); *A61Q 15/00* (2013.01); *A61Q 19/10* (2013.01); *C07C 29/143* (2013.01); *C07C 29/145* (2013.01); *C07C 31/125* (2013.01); *C07C 45/66* (2013.01); *C07C 45/72* (2013.01); *C11D 3/50* (2013.01); *D06M 13/005* (2013.01); *D06M 13/144* (2013.01)

(58) Field of Classification Search
CPC ....................................................... A61K 8/34
See application file for complete search history.

(56) References Cited

U.S. PATENT DOCUMENTS

| | | | |
|---|---|---|---|
| 3,452,105 A | 6/1969 | Marbet | |
| 4,021,461 A * | 5/1977 | Henrick | ................. C07C 29/42 554/224 |
| 4,198,532 A | 4/1980 | Ochsner | |
| 4,892,966 A | 1/1990 | Wild | |
| 2004/0242452 A1 | 12/2004 | Shoji et al. | |
| 2008/0207481 A1 | 8/2008 | Meine et al. | |
| 2009/0081755 A1 * | 3/2009 | Schmiedel | ............... C11D 3/50 435/183 |
| 2011/0081393 A1 | 4/2011 | Komatsuki et al. | |

FOREIGN PATENT DOCUMENTS

| | | |
|---|---|---|
| DE | 10 2010 002 104 A1 | 8/2011 |
| JP | 54-27506 | 3/1979 |
| JP | 08-048648 | 2/1996 |
| JP | 09-048718 | 2/1997 |
| JP | 2000-169877 | 6/2000 |
| JP | 2001-098300 | 4/2001 |
| JP | 2004-043618 | 2/2004 |
| JP | 2004-161948 | 6/2004 |
| JP | 2009-507112 | 2/2009 |
| JP | 2010-065233 | 3/2010 |
| JP | 2012-197534 | 10/2012 |
| JP | 2012-233042 | 11/2012 |
| WO | WO 2010/091969 A1 | 8/2010 |
| WO | 2011-135487 | 11/2011 |

OTHER PUBLICATIONS

Extended Search Report issued Nov. 27, 2015 in European Patent Application No. 13796988.7.
International Search Report issued Aug. 20, 2013 in PCT/JP13/065058, filed May 30, 2013.
Anderson, G., et al. "Volatile Compounds from the interdigital Gland of Reindeer", Journal of Chemical Ecology., vol. 5, No. 3, pp. 321-333, 1979.
Thomas, H., et al. "Wissenschaftlicher Teil", Untersuchungen in der gruppe der Riechstoffe—(Ans dem Phramazeutischen Institut der Universitat Berlin)., vol. 263, pp. 241-252, 1925.

* cited by examiner

Primary Examiner — Adam C Milligan
Assistant Examiner — Sarah Alawadi
(74) Attorney, Agent, or Firm — Oblon, McClelland, Maier & Neustadt, L.L.P.

(57) ABSTRACT

Provided is a fragrance composition containing a compound that is highly harmonious with other various fragrances and that can impart a stronger floral feeling by being blended. A fragrance composition containing 3,6-dimethyl-heptane-2-ol. The fragrance composition may further contain at least one selected from the group consisting of, for example, 7-methyloctane-3-ol, esters, carbonates, aldehydes, ethers, lactones, and alcohols other than 3,6-dimethylheptane-2-ol.

17 Claims, No Drawings

FRAGRANCE COMPOSITION

CROSS REFERENCE TO RELATED APPLICATION

This application is a 371 of PCT/JP2013/065058, filed on May 30, 2013, and claims priority to Japanese Patent Application No. 2012-126075, filed on Jun. 1, 2012.

TECHNICAL FIELD

The present invention relates to a fragrance composition containing 3,6-dimethylheptane-2-ol.

BACKGROUND ART

Fragrance is an important element that produces, for example, preference, a sense of luxury, a sense of ease, and expectations for the effect for products and the like. Furthermore, a distinctive fragrance provides a product differentiation effect and the capacity for attracting customers. Particularly, floral fragrance notes are preferred for toiletry products.

Alcohols such as linalool, citronellol, and geraniol are known as fragrance materials that impart floral fragrance notes.

On the other hand, in order to control, for example, a long-lasting property and balance of a fragrance, generally, a fragrance is imparted to a product using a fragrance composition in which a plurality of fragrance materials are mixed together. It is required for the fragrance materials composing the fragrance composition to be highly harmonious with other fragrance materials.

Examples of commercial products of alcohols include 3,4,5,6,6-pentamethylheptane-2-ol, which is sold as Kohinol (product name) by IFF.

Furthermore, Patent Document 1 discloses that 2,5,7-trimethyl-3-octanol and 2,4-dimethyl-8-nonanol each are useful as a fragrance and have a fruit-like fragrance note.

Patent Document 2 discloses that, for example, 3-butyl-6-methylheptane-2-ol is useful as a fragrance and has a green narcissus and aromatic gentian like fragrance notes.

Patent Document 3 discloses that 3-hydroxy-7-isobutyl-1,6-octadiene and derivatives thereof each are useful as a fragrance and have a fresh grass-like fragrance note.

Very roughly speaking, fragrance materials have similar fragrance notes when they have similar structures to each other, but there are many exceptions. Particularly, when a plurality of substituents are combined to change the structure, it is difficult to predict how the fragrance note will change and it is also difficult to predict the harmonicity with other fragrance materials.

PRIOR ART DOCUMENTS

Patent Documents

[Patent Document 1] JP 54(1979)-27506 A
[Patent Document 2] WO 2011/135487
[Patent Document 3] U.S. Pat. No. 3,452,105

DISCLOSURE OF INVENTION

Problem to be Solved by the Invention

Some fragrance materials may interfere with other fragrance components and thereby may change fragrance notes or weaken them mutually. Therefore, in order to increase flexibility in blending odors, it is desired to increase the number of types of fragrance materials. Particularly, fragrance compositions that have fresh floral fragrance notes with a feeling of cleanliness and that are used suitably to impart fragrances to toiletry products have been desired.

Therefore, it is an object of the present invention to provide a fragrance composition that has excellent harmonicity with various other fragrances and can impart a stronger floral feeling by being blended.

Means for Solving Problem

The present inventors found that saturated aliphatic alcohol with a specific structure has excellent harmonicity with various fragrances and imparts a stronger floral feeling by being blended, and thereby the present invention was completed.

That is, it is an object of the present invention to provide a fragrance composition containing 3,6-dimethylheptane-2-ol.

Effects of the Invention

The fragrance composition of the present invention contains 3,6-dimethylheptane-2-ol and therefore has excellent harmonicity with various other fragrances and can impart a stronger floral feeling by being blended.

DESCRIPTION OF THE INVENTION

Method of Producing 3,6-Dimethylheptane-2-ol

The 3,6-dimethylheptane-2-ol (represented by Formula (I) below. In the present description, it may also be referred to as Compound (I).) of the present invention can be synthesized using a common organic chemical reaction. The method of producing it is not limited. For example, Compound (I) can be produced using a method including a step of obtaining Compound (I) by carrying out a cross aldol reaction using isovaleraldehyde (represented by Formula (XI) below. In the present description, it may also be referred to as Compound (XI).) and 2-butanone (represented by Formula (X) below. In the present description, it may also be referred to as Compound (X).), and then dehydrating and reducing it (see Scheme 1).

Scheme 1

[Chemical Formula 1]

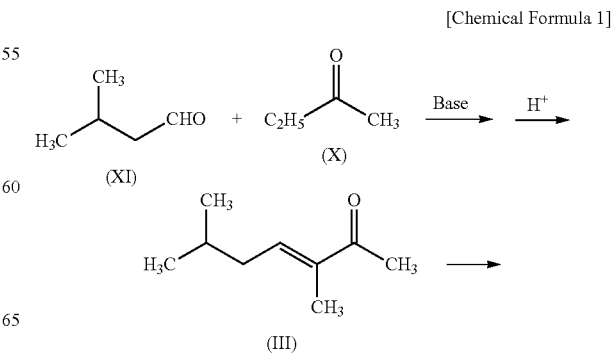

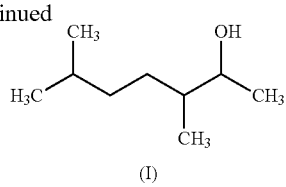

(I)

In the aforementioned production method, first, the cross aldol reaction is carried out using isovaleraldehyde (XI) and 2-butanone (X) in the presence of a base catalyst. The base catalyst is preferably alkali metal hydroxide, more preferably sodium hydroxide. The reaction is carried out at a temperature of, for example, 15 to 30° C., for example, 1 to 60 hours.

Particularly, from the viewpoint of making the cross aldol reaction proceed with a good yield, it is preferable to further add water to the reaction solution.

Subsequently, the product thus obtained is dehydrated. Preferably, the dehydration is carried out at the temperature not lower than the boiling point of water, with, for example, phosphoric acid being added to the reaction solution. When the pressure of the reaction system is changed, it is preferable that the dehydration be carried out at the temperature not lower than the boiling point of water that is obtained under such pressure. When it is carried out at 1 atm (101 kPa), it is preferable that the product be dehydrated while being heated, for example, at 110 to 160° C.

The dehydration allows 3,6-dimethylhept-3-en-2-one (represented by Formula (III) above. In the present description, it may also be referred to as Compound (III).) to be obtained.

In the cross aldol reaction, when 7-methyloct-4-en-3-one (represented by Formula (IV) below. In the present description, it may also be referred to as Compound (IV).) is obtained together with Compound (III) (see Scheme 2), Compound (III) may be separated from Compound (IV) by precision distillation or a combination of a silica gel column and distillation. This separation allows Compound (III) with a higher purity to be obtained. Alternatively, adjusting the conditions for the separation allows a mixture of Compound (III) and Compound (IV) at a specific ratio to be obtained.

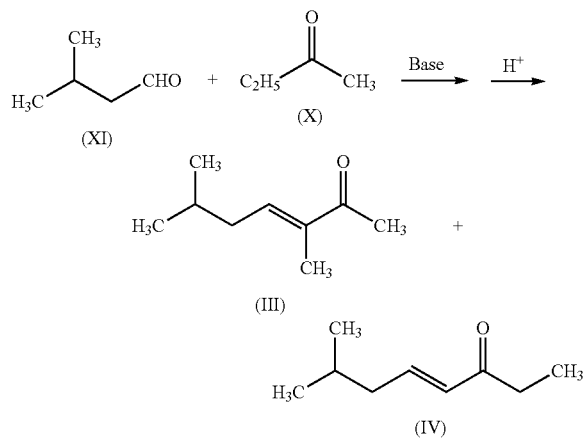

Subsequently, Compound (III) is reduced and thereby Compound (I) is obtained. The reduction method is not particularly limited as long as it is a general reduction method. However, from the view point of increasing the purity, a hydrogenation method using a noble metal catalyst is preferred. Specifically, reduction can be carried out by hydrogenation under a hydrogen atmosphere in the presence of a noble metal catalyst such as ruthenium, palladium, or platinum. Hydrogenation is carried out under a hydrogen pressure of, for example, 0.1 to 5 MPa preferably at a temperature of 50 to 170° C., more preferably at a temperature of 60 to 160° C., and further preferably at a temperature of 80 to 160° C. Furthermore, the reaction time for hydrogenation is, for example, 3 to 80 hours.

Thus, Compound (I) can be obtained at a high purity. Compound (I) thus obtained has floral, citrus, and slightly woody fragrance notes.

On the other hand, when reduction is carried out using a mixture of Compound (III) and Compound (IV) without separating them, a mixture of Compound (I) and 7-methyloctane-3-ol (represented by Formula (II) below. In the present description, it may also be referred to as Compound (II).) can be obtained (see Scheme 3).

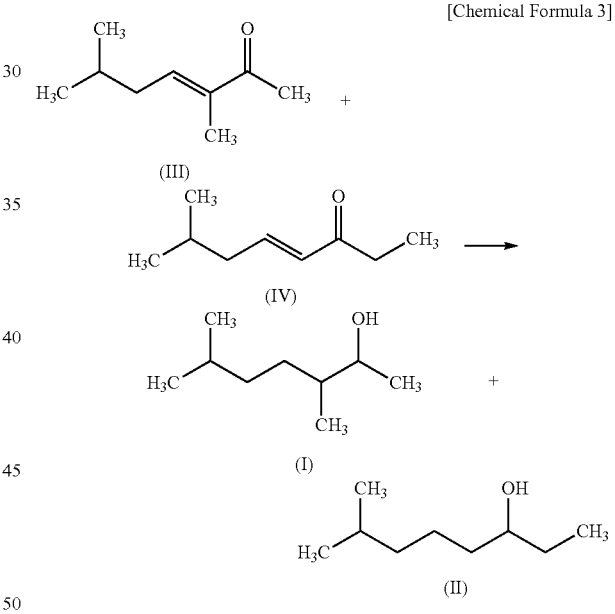

[Fragrance Composition]

As described above, the fragrance composition of the present invention contains 3,6-dimethylheptane-2-ol (Compound (I)). The amount of Compound (I) contained in the fragrance composition is preferably 0.01 to 100% by mass, more preferably 0.1 to 15% by mass, and further preferably 0.3 to 5% by mass. When containing 0.01 to 100% by mass of Compound (I), the fragrance composition can be imparted with a stronger floral feeling.

Furthermore, the fragrance composition of the present invention may further contain 7-methyloctane-3-ol (Compound (II)). When the fragrance composition of the present invention further contains Compound (II), the total amount of Compound (I) and Compound (II) contained in the fragrance composition is preferably 0.01 to 100% by mass, more preferably 0.1 to 15% by mass, and further preferably 0.3 to 5% by mass. When containing Compound (I) and Compound (II) in a total amount of 0.01 to 100% by mass, the fragrance composition can be imparted with a stronger floral feeling and fruitiness.

Moreover, the fragrance composition of the present invention can contain, as a fragrance other than Compound (I), another fragrance component that is commonly used or a formulated perfume with a desired composition. When containing a fragrance other than Compound (I), the fragrance composition of the present invention can be imparted with an odor of, for example, a floral tone, a bouquet tone, a hyacinth tone, a geranium tone, a rose tone, a bergamot tone, an orchid tone, or a lily of the valley tone (muguet).

When the fragrance composition of the present invention further contains Compound (II), the ratio (weight ratio) of Compound (I) and Compound (II) contained therein (Compound (D/Compound (II)) is preferably 70/30 to 99.9/0.1, more preferably 80/20 to 99/1, further preferably 80/20 to 98/2, still further preferably 80/20 to 95/5, and yet further preferably 90/10 to 95/5 from the viewpoint of imparting excellent fruitiness, with floral and citrus fragrance notes being maintained.

Furthermore, from the viewpoint of imparting a strong floral odor with excellent woodiness, the ratio is preferably 80/20 to 100/0, further preferably 90/10 to 100/0, still further preferably 95/5 to 100/0, and yet further preferably 95/5 to 99/1.

In fabric treatment compositions such as a softener, cleaner compositions, or cosmetics such as hair cosmetics of the present invention, when both Compound (I) and Compound (II) are contained, the ratio (weight ratio) of Compound (I) and Compound (II) contained therein is further preferably 90/10 to 95/5 from the viewpoint of imparting a fresh floral fragrance note with a feeling of cleanliness, i.e. a fresh feeling.

When the fragrance composition of the present invention further contains Compound (II), the ratio (mass ratio) of Compound (I) and Compound (II) contained therein (Compound (I)/Compound (II)) is preferably 70/30 to 99.9/0.1, more preferably 80/20 to 99/1, further preferably 80/20 to 98/2, still further preferably 80/20 to 95/5, and yet further preferably 90/10 to 95/5 from the viewpoint of imparting excellent fruitiness, with floral and citrus fragrance notes being maintained.

Furthermore, from the viewpoint of imparting excellent woodiness to a strong floral odor, the ratio is preferably 80/20 to 100/0, further preferably 90/10 to 100/0, still further preferably 95/5 to 100/0, and yet further preferably 95/5 to 99/1.

In fabric treatment compositions such as a softener, cleaner compositions, or cosmetics such as hair cosmetics of the present invention, when both Compound (I) and Compound (II) are contained, the ratio (mass ratio) of Compound (I) and Compound (II) contained therein is further preferably 90/10 to 95/5 from the viewpoint of imparting a fresh floral fragrance note with a feeling of cleanliness, i.e. a fresh feeling.

Furthermore, the fragrance composition of the present invention contains 7-methyloctane-3-ol (Compound (II)). The amount of Compound (II) contained in the fragrance composition is preferably 0.01 to 99% by mass, more preferably 0.1 to 15% by mass, and further preferably 0.3 to 5% by mass. Compound (II) contained in an amount of 0.01 to 99% by mass allows the fragrance composition to be imparted with a stronger floral feeling.

In the fragrance composition of the present invention, examples of other fragrances that can be used in combination with Compound (I) and/or Compound (II) include alcohols other than Compound (I) and Compound (II), hydrocarbons, phenols, esters, carbonates, aldehydes, ketones, acetals, ethers, carboxylic acids, lactones, nitriles, Schiff bases, and fragrance components such as natural essential oils and natural extracts.

Among them, alcohols other than Compound (I) and Compound (II), esters, carbonates, aldehydes, ketones, ethers, and lactones are preferable, and particularly, alcohols other than Compound (I) and Compound (II) and esters are more preferable.

Examples of alcohols other than Compound (I) and Compound (II) include terpene alcohols, aromatic alcohols, and aliphatic alcohols. Among them, terpene alcohols and aromatic alcohols are preferable.

Examples of terpene alcohols include linalool, citronellol, geraniol, nerol, terpineol, α-terpineol, dihydromyrcenol, farnesol, nerolidol, cedrol, menthol, and borneol.

Examples of aromatic alcohols include phenylethyl alcohol, benzyl alcohol, dimethyl benzyl carbinol, phenylethyl dimethyl carbinol, and phenyl hexanol.

Examples of aliphatic alcohols include cis-3-hexenol, 1-(2,2,6-trimethylcyclohexyl)-3-hexanol, Amber Core (Trade Name of Kao Corporation, 1-(2-tert-butyl cyclohexyloxy)-2-butanol), Sandalmysore Core (Trade Name of Kao Corporation, 2-methyl-4-(2,2,3-trimethyl-3-cyclopenten-1-yl)-2-buten-1-ol), Magnol (Trade Name of Kao Corporation, a mixture containing, as a main component, 3(4)-(5-ethyl-bicyclo[2.2.1]heptyl-2)-cyclohexanol), Undecavertol (Trade Name of Givaudan Roure K.K., 4-methyl-3-decene-5-ol), and isobornylcyclohexanol.

Examples of hydrocarbons include limonene, α-pinene, β-pinene, terpinene, cedrene, longifolene, and valencene.

Examples of phenols include guaiacol, eugenol, isoeugenol, thymol, p-cresol, vanillin, and ethyl vanillin.

Examples of esters include formate ester, acetate ester, propionate ester, butyrate ester, valerate ester, hexanoate ester, heptanoate ester, nonenoate ester, benzoate ester, cinnamate ester, salicylate ester, brasylate ester, tiglate ester, jasmonate ester, glycidate ester, and anthranilate ester.

Among these esters, acetate ester, propionate ester, salicylate ester, and jasmonate ester are used preferably.

Examples of formate ester include linalylformate, citronellylformate, and geranylformate.

Examples of acetate ester include hexyl acetate, cis-3-hexenyl acetate, linalyl acetate, citronellyl acetate, geranyl acetate, neryl acetate, terpinyl acetate, nopyl acetate, bornyl acetate, isobornyl acetate, acetyl eugenol, acetyl isoeugenol, o-tert-butylcyclohexyl acetate, p-tert-butylcyclohexyl acetate, tricyclodecenyl acetate, benzyl acetate, phenylethyl acetate, styralyl acetate, cinnamyl acetate, dimethylbenzylcarbinyl acetate, phenylethyl phenyl acetate 3-pentyltetrahydropyran-4-yl acetate, and p-cresyl phenyl acetate.

Examples of propionate ester include citronellyl propionate, tricyclodecenyl propionate, allylcyclohexyl propionate, ethyl 2-cyclohexyl propionate, benzyl propionate, and styralyl propionate.

Examples of butyrate ester include citronellyl butyrate, dimethylbenzylcarbinyl n-butyrate, and tricyclodecenyl isobutyrate.

Examples of valerate ester include methyl valerate, ethyl valerate, butyl valerate, amyl valerate, benzyl valerate, and phenylethyl valerate. Examples of hexanoate ester include methyl hexanoate, ethyl hexanoate, allyl hexanoate, linalyl hexanoate, and citronellyl hexanoate.

Examples of heptanoate ester include methyl heptanoate and allyl heptanoate.

Examples of nonenoate ester include methyl 2-nonenoate, ethyl 2-nonenoate, and ethyl 3-nonenoate.

Examples of benzoate ester include methyl benzoate, benzyl benzoate, and 3,6-dimethyl benzoate.

Examples of cinnamate ester include methyl cinnamate and benzyl cinnamate.

Examples of salicylate ester include methyl salicylate, n-hexyl salicylate, cis-3-hexenyl salicylate, cyclohexyl salicylate, and benzyl salicylate.

Furthermore, examples of brasylate ester include ethylene brassylate.

Examples of tiglate ester include geranyl tiglate, 1-hexyl tiglate, and cis-3-hexenyl tiglate.

Examples of jasmonate ester include methyl jasmonate and methyl dihydrojasmonate.

Examples of glycidate ester include methyl 2,4-dihydroxy-ethylmethylphenyl glycidate and 4-methylphenylethyl glycidate.

Examples of anthranilate ester include methyl anthranilate, ethyl anthranilate, and dimethyl anthranilate.

Furthermore, examples of other esters include methyl atrarate, allyl cyclohexyl glycolate, Fruitate (Trade Name of Kao Corporation, ethyl tricyclo[5.2.1.0]decan-2 carboxylate), Poirenate (Trade Name of Kao Corporation, ethyl 2-cyclohexyl propionate), Peranat (Trade Name of Kao Corporation, 2-Methylpentyl 2-methylvalerate), Melusat (Trade Name of Kao Corporation, Ethyl 3,5,5-trimethyl hexanoate), and Irotyl (Trade Name of Kao Corporation, ethyl 2-ethylcapronate).

Examples of carbonates include Liffarome (Trade Name of IFF, cis-3-hexenyl methyl carbonate), Jasmacyclat (Trade Name of Kao Corporation, methyl cyclooctyl carbonate), and Floramat (Trade Name of Kao Corporation, ethyl 2-tert-butylcyclohexyl carbonate).

Examples of aldehydes include n-octanal, n-nonanal, n-decanal, n-dodecanal, 2-methyl undecanal, 10-undecenal, citronellal, citral, hydroxycitronellal, Triplal (Trade Name of IFF, 2,4-Dimethyl-3-cyclohexene-1-carboxaldehyde), Cyclovertal (Trade Name of Kao Corporation, dimethyl-3-cyclohexenyl-1-carboxaldehyde), benzaldehyde, phenylacetaldehyde, phenyl propyl aldehyde, cinnamaldehyde, dimethyltetrahydrobenzaldehyde, Bourgeonal (Trade Name of Givaudan, 3-(4 tert-Butylphenyl)propanal), Lyral (Trade Name of IFF, hydroxy myrac aldehyde), Pollenal II (Trade Name of Kao Corporation, 2-cyclohexyl propanal), Lilial (Trade Name of Givaudan, p-tert-butyl-α-methylhydrocinnamaldehyde), p-isopropyl-α-methylhydrocinnamaldehyde, Floralozone (Trade Name of IFF, 3-(o-(and p-)ethylphenyl)-2,2-dimethylpropionaldehyde), α-amyl cinnamaldehyde, α-hexyl cinnamaldehyde, heliotropin, and Helional (Trade Name of IFF, alpha-methyl-1,3-benzodioxole-5-propanal).

Examples of ketones include α-ionone, β-ionone, γ-ionone, α-methyl ionone, β-methyl ionone, γ-methyl ionone, damascenone, methyl heptenone, 4-methylene-3,5,6,6-tetramethyl-2-heptanone, acetophenone, amyl cyclopentanone, dihydrojasmone, rose ketone, carvone, menthone, camphor, acetyl cedrene, isolongifolanone, nootkatone, benzyl acetone, anisyl acetone, methyl β-naphthyl ketone, 2,5-dimethyl-4-hydroxy-3(2H)-furanone, maltol, muscone, civetone, cyclopentadecanone, Calone (Trade Name of Firmenich, 7-methyl-3,5-dihydro-2H-benzodioxepin-3-one), raspberry ketone, methyl-b-naphthyl ketone, and heliotropyl acetone.

Examples of acetals include acetaldehyde ethylphenylpropyl acetal, citral diethyl acetal, phenylacetaldehyde glyceryl acetal, ethyl acetoacetate ethylene glycol acetal, Boisambrene Forte (Trade Name of Kao Corporation), and Troenan (Trade Name of Kao Corporation).

Examples of ethers include ethyllinalool, cedryl methyl ether, estragole, anethole, β-naphthyl methyl ether, β-naphthyl ethyl ether, limonene oxide, rose oxide, nerol oxide, 1,8-cineole, rose furan, Ambroxan (Trade Name of Kao Corporation, dodecahydro-3a,6,6,9a-tetramethyl naphto[2,1-b]furan), Herbavert (Trade Name of Kao Corporation, 3,3,5-trimethylcyclohexyl-ethyl-ether), Galaxolide (Trade Name of IFF, hexamethylhexahydrocyclopentabenzopyran), and phenylacetaldehyde dimethyl acetal.

Examples of carboxylic acids include benzoic acid, phenylacetic acid, cinnamic acid, hydrocinnamic acid, butyric acid, and 2-hexenoic acid.

Examples of lactones include γ-decalactone, δ-decalactone, γ-valerolactone, γ-nonalactone, γ-undecalactone, δ-hexalactone, γ-jasmolactone, whisky lactone, coumarin, cyclopentadecanolide, cyclohexadecanolide, ambrettolide, 11-oxahexadecanolide, and butylidenephthalide.

Examples of nitriles include geranyl nitrile, citronellyl nitrile, and dodecanenitrile.

Examples of Schiff bases include aurantiol and ligantral.

Examples of natural essential oils and natural extracts include orange, lemon, lime, bergamot, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamon, cedar, cypress, vetiver, patchouli, lemongrass, labdanum, and grapefruit.

The amount of these other fragrances to be contained except for Compound (I) can be selected suitably depending on, for example, the type of the formulated perfume as well as the type and intensity of the intended odor. The amount of each of them contained in the fragrance composition is preferably 0.0001 to 99.99% by mass, more preferably 0.001 to 80% by mass. Furthermore, the total amount of the other fragrances contained in the fragrance composition is preferably 5 to 99.99% by mass, more preferably 50 to 99.95% by mass.

When the fragrance composition of the present invention further contains Compound (II), the amount of the other fragrances contained except for Compound (I) and Compound (II) can be selected suitably depending on, for example, the type of the formulated perfume as well as the type and intensity of the intended odor. The amount of each of them contained in the fragrance composition is preferably 0.0001 to 99.99% by mass, more preferably 0.001 to 80% by mass. Furthermore, the total amount of the other fragrances contained in the fragrance composition is preferably 5 to 99.99% by mass, more preferably 50 to 99.95% by mass.

Moreover, when the fragrance composition of the present invention contains Compound (II), the amount of the other fragrances contained except for Compound (II) can be selected suitably depending on, for example, the type of the formulated perfume as well as the type and intensity of the intended odor. The amount of each of them contained in the fragrance composition is preferably 0.0001 to 99.99% by mass, more preferably 0.001 to 80% by mass. Furthermore, the total amount of the other fragrances contained in the fragrance composition is preferably 5 to 99.99% by mass, more preferably 50 to 99.95% by mass.

The fragrance composition of the present invention can contain an oil, which itself has no odor, to be used as a base that allows 3,6-dimethylheptane-2-ol (Compound (I)), 7-methyloctane-3-ol (Compound (II)), and the other fragrance materials to be contained therein. Such an oil allows a fragrance component to be mixed uniformly, to be easily mixed into a product, and to easily impart a suitable intensity of fragrance. Specific examples of such an oil include polyhydric alcohols such as ethylene glycol, propylene glycol, butylene glycol, and dipropylene glycol, esters such as isopropyl myristate, dibutyl adipate, and diethyl sebacate, and hydrocarbons such as liquid paraffin and squalane. The amount of such an oil to be contained in the fragrance composition is preferably 1 to 95% by mass, more preferably 10 to 80% by mass, and further preferably 15 to 50% by mass.

Furthermore, the fragrance composition of the present invention may contain a surfactant such as polyoxyethylene alkyl ether or sorbitan fatty acid ester.

[Use as Fragrance Component]

A fragrance composition containing 3,6-dimethylheptane-2-ol (Compound (I)), a fragrance composition containing Compound (I) and 7-methyloctane-3-ol (Compound (II)), and a fragrance composition containing 7-methyloctane-3-ol (Compound (II)) according to the present invention can be used, as fragrance components of various types of products, as formulated perfumes or fragrance materials with a strong floral feeling. Therefore, it is an object of the present invention to provide a method of using, as a fragrance, a fragrance composition containing 3,6-dimethylheptane-2-ol (Compound (I)), a fragrance composition containing Compound (I) and 7-methyloctane-3-ol (Compound (II)), and a fragrance composition containing 7-methyloctane-3-ol (Compound (II)). For the method of using said compounds, they each can be contained, alone or in combination with other components, in the bases of toiletry products such as soaps, cosmetics, hair cosmetics, detergents, softeners, spray products, air fresheners, perfumes, and bath agents. Accordingly, it is an object of the present invention to provide a method of using a fragrance composition containing 3,6-dimethylheptane-2-ol (Compound (I)), a fragrance composition containing Compound (I) and 7-methyloctane-3-ol (Compound (II)), and a fragrance composition containing 7-methyloctane-3-ol (Compound (II)), as a fragrance for toiletry products such as soaps, cosmetics, hair cosmetics, detergents, softeners, spray products, air fresheners, perfumes, and bath agents.

In the aforementioned method of using the fragrance compositions, when the fragrance composition contains 3,6-dimethylheptane-2-ol (Compound (I)), the amount of Compound (I) to be used is preferably 0.01 to 100% by mass, more preferably 0.1 to 15% by mass, and further preferably 0.3 to 5% by mass, with respect to the whole fragrance composition. Compound (I) contained in an amount of 0.01 to 100% by mass can impart a stronger floral feeling.

In the aforementioned method of using the fragrance compositions, when the fragrance composition contains Compound (I) and 7-methyloctane-3-ol (Compound (II)), the total amount of Compound (I) and Compound (II) to be contained is preferably 0.01 to 100% by mass, more preferably 0.1 to 15% by mass, and further preferably 0.3 to 5% by mass, with respect to the whole fragrance composition. When the total amount of Compound (I) and Compound (II) contained therein is 0.01 to 100% by mass, the fragrance composition can be imparted with a stronger floral feeling and fruitiness.

Furthermore, in the aforementioned method of using the fragrance compositions, when the fragrance composition contains 7-methyloctane-3-ol (Compound (II)), the amount of Compound (II) is preferably 0.01 to 100% by mass, more preferably 0.1 to 15% by mass, and further preferably 0.3 to 5% by mass, with respect to the whole fragrance composition. Compound (II) contained in an amount of 0.01 to 100% by mass can impart a stronger floral feeling and fruitiness.

Particularly, it is preferable that the fragrance composition containing 3,6-dimethylheptane-2-ol (Compound (I)), the fragrance composition containing Compound (I) and 7-methyloctane-3-ol (Compound (II)), and the fragrance composition containing 7-methyloctane-3-ol (Compound (II)) of the present invention be used to treat hairs or fabrics such as clothing to impart floral-like fragrances. Examples of the products, for which they can be used preferably as a fragrance component, include hair cosmetics such as shampoos and hair conditioners as well as softeners for clothing.

Accordingly, the present invention also provides a cleaner composition containing a fragrance composition of the present invention, a cosmetic containing a fragrance composition of the present invention, a fabric treatment composition containing a fragrance composition of the present invention, a fragrant deodorant containing a fragrance composition of the present invention, and a cleaning nonwoven fabric containing a fragrance composition of the present invention.

The cleaner composition of the present invention is preferably a body cleaner composition, a cleaner composition for clothing, or a cleaner composition for hard surfaces, more preferably a body cleaner composition or a cleaner composition for clothing, and further preferably a cleaner composition for clothing. Furthermore, examples of the cleaner composition of the present invention include a powder cleaner composition and a liquid cleaner composition, and it is preferably a liquid cleaner composition.

Examples of the body cleaner composition include a skin cleaner composition and a hair cleaner composition, and it is preferably a skin cleaner composition.

Examples of the cleaner composition for hard surfaces include an all purpose cleaner and a cleaner composition for tableware.

The fabric treatment composition of the present invention is preferably a softener.

The cosmetic of the present invention is preferably a perfume, a body cosmetic, or a hair cosmetic.

The softener of the present invention contains, for example, quaternary ammonium salt and a fragrance composition of the present invention. The above-mentioned softener may further contain a germicide, a viscosity modifier, a pH adjuster, a solvent, etc.

For the quaternary ammonium salt, any conventionally known one can be used. Example thereof include octyl trimethyl ammonium chloride, dodecyl trimethyl ammonium chloride, hexadecyl trimethyl ammonium chloride, beef tallow trimethyl ammonium chloride, coconut oil trimethyl ammonium chloride, octyl dimethyl benzyl ammonium chloride, decyl dimethyl benzyl ammonium chloride, dioctadecyl dimethyl ammonium chloride, distearoyloxyethyl dimethyl ammonium chloride, dioleoyloxyethyl dimethyl ammonium chloride, N-stearoyl oxy ethyl-N,N-dimethyl-N-(2-hydroxyethyl)ammonium methyl sulfate, N,N-distearoyl oxy ethyl-N-methyl-N-(2-hydroxyethyl) ammonium methyl sulfate, N-oleoyloxyethyl-N,N-dimethyl-N-(2-hydroxyethyl)ammonium methyl sulfate, distearyl methylamine hydrochloride, dioleyl methylamine hydrochloride, distearyl methylamine sulfate, N-(3-octadecanoylaminopropyl)-N-(2-octadecanoyloxyethyl-N-methyl-aminehydrochloride, methyl-1-beef tallow amide ethyl-2-beef tallow alkyl imidazolinium methyl sulfate, methyl-1-hexadecanoyl amide ethyl-2-pentadecyl imidazolinium chloride, ethyl-1-octadecenoyl amide ethyl-2-heptadecenyl imidazolinium ethyl sulfate, 1-octadecanoyl aminoethyl-2-heptadecyl imidazoline hydrochloride, 1-octadecenoyl aminoethyl-2-heptadecenyl imidazoline hydrochloride, and N,N-di[2-(alkanoyloxy)-ethyl]-N-(2-hydroxyethyl)-N-methyl ammonium sulfate. One of these can be used alone or two or more of them can be used in combination.

Examples of the above-mentioned germicide include alcohols having 1 to 8 carbon atoms, benzoic acids, and phenols. Specific examples thereof include ethanol, propylene glycol, benzyl alcohol, salicylic acid, methyl p-hydroxybenzoate, and cresol.

Inorganic or organic salts (excluding a quaternary ammonium salt) can be used as the viscosity modifier mentioned above. Specific examples thereof include sodium chloride, potassium chloride, calcium chloride, magnesium chloride, aluminum chloride, sodium sulfate, magnesium sulfate, potassium sulfate, sodium nitrate, magnesium nitrate, sodium p-toluenesulfonate, sodium glycolate, sodium acetate, potassium acetate, potassium glycolate, and sodium lactate. Preferably, the viscosity modifier is calcium chloride or magnesium chloride.

The softener of the present invention contains water, and generally the remainder of the composition is water. The water is preferably ion exchanged water or distilled water. Preferably, the softener of the present invention has a pH of 1.5 to 6 at 20° C. From the viewpoints of antisepsis/bactericidal activity, the lower the pH is, the better. However, an excessively low pH may cause decomposition of components that are generally mixed into compositions. Therefore, the pH is more preferably 1.5 to 5 and further preferably 2 to 4.5.

Any inorganic or organic acid and alkali can be used for adjusting the pH of the softener of the present invention.

Furthermore, known components that usually are mixed in a softener as other optional components in addition to the above-mentioned components can be mixed in the softener of the present invention in a range that does not hinder the effects of the present invention. Examples of the optional components that can be mixed include: higher fatty acids such as stearic acid, oleic acid, and palmitic acid or esters thereof formed with lower alcohols; nonionic surfactants such as fatty acid glycerol ester, which is an ester of, for example, stearic acid and glycerol; higher alcohols such as stearyl alcohol, palmityl alcohol, and oleyl alcohol; and low-temperature stabilizers such as ethylene glycol and glycerol. In addition to these, for example, urea, pigments, a cellulose derivative, an ultraviolet absorber, and a fluorescent brightener can be mixed.

It is preferable that the cleaner composition of the present invention contain an anionic surfactant other than a fragrance composition containing 3,6-dimethylheptane-2-ol and/or 7-methyloctane-3-ol. Furthermore, a nonionic surfactant, a pH adjuster, a viscosity modifier, a solvent, an oil, a preservative, water, etc. can be mixed thereinto.

In the perfume of the present invention, a solvent, water, etc. can be mixed thereinto other than a fragrance composition containing 3,6-dimethylheptane-2-ol and/or 7-methyloctane-3-ol.

The present invention provides 3,6-dimethylheptane-2-ol (Compound (I)). The 3,6-dimethylheptane-2-ol (Compound (I)) has floral, citrus, and slightly woody fragrance notes as described above. Therefore, the present invention is a method of using 3,6-dimethylheptane-2-ol (Compound (I)) as a fragrance component. Furthermore, the present invention provides a method of using 3,6-dimethylheptane-2-ol (Compound (I)) as a fragrance component.

With respect to the above-mentioned embodiment, the present invention further discloses the following fragrance compositions, production method, method of using fragrance compositions, and use thereof.

<1> A fragrance composition containing 3,6-dimethylheptane-2-ol.

<2> The fragrance composition according to the item <1>, wherein the amount of 3,6-dimethylheptane-2-ol contained therein is preferably 0.01 to 100% by mass, more preferably 0.1 to 15% by mass, and further preferably 0.3 to 5% by mass.

<3> The fragrance composition according to the item <1> or <2>, further containing 7-methyloctane-3-ol.

<4> The fragrance composition according to the item <2> or <3>, wherein the total amount of 3,6-dimethylheptane-2-ol and 7-methyloctane-3-ol contained therein is preferably 0.01 to 100% by mass, more preferably 0.1 to 15% by mass, and further preferably 0.3 to 5% by mass.

<5> The fragrance composition according to any one of the items <2> to <4>, wherein 3,6-dimethylheptane-2-ol and 7-methyloctane-3-ol are contained at a ratio (3,6-dimethylheptane-2-ol/7-methyloctane-3-ol) of 70/30 to 99.9/0.1, preferably 80/20 to 99/1, more preferably 80/20 to 95/5, and further preferably 90/10 to 95/5 (all in weight ratio).

<6> A fragrance composition containing 7-methyloctane-3-ol.

<7> The fragrance composition according to the item <6>, wherein the amount of 7-methyloctane-3-ol contained therein is preferably 0.01 to 99% by mass, more preferably 0.1 to 15% by mass, and further preferably 0.3 to 5% by mass.

<8> The fragrance composition according to any one of the items <1> to <7>, further containing at least one selected from alcohols other than 3,6-dimethylheptane-2-ol and 7-methyloctane-3-ol, esters, carbonates, aldehydes, ketones, ethers, and lactones.

<9> The fragrance composition according to the item <8>, wherein the esters are at least one selected from the group consisting of acetate ester, propionate ester, salicylate ester, jasmonate ester, methyl atrarate, Fruitate, and Poirenate.

<10> The fragrance composition according to the item <8> or <9>, wherein the carbonates are Liffarome.

<11> The fragrance composition according to any one of the items <8> to <10>, wherein the aldehydes are at least one selected from the group consisting of Triplal, Bourgeonal, Lilial, Floralozone, α-hexyl cinnamaldehyde, and Helional.

<12> The fragrance composition according to any one of the items <8> to <11>, wherein the ketones are at least one selected from the group consisting of β-ionone, damascenone, muscone, Calone, raspberry ketone, methyl-β-naphthyl ketone, and heliotropyl acetone.

<13> The fragrance composition according to any one of the items <8> to <12>, wherein the ethers are at least one selected from the group consisting of rose oxide, Ambroxan, Galaxolide, and phenylacetaldehyde dimethyl acetal.

<14> The fragrance composition according to any one of the items <8> to <13>, wherein the lactones are ambrettolide.

<15> The fragrance composition according to any one of the items <1> to <14>, wherein the alcohols fragrance other than 3,6-dimethylheptane-2-ol and 7-methyloctane-3-ol are at least one selected from the group consisting of terpene alcohol and aliphatic alcohol.

<16> The fragrance composition according to any one of the items <1> to <15>, further containing an oil.

<17> The fragrance composition according to any one of the items <1> to <15>, further containing a surfactant.

<18> A fabric treatment composition (preferably a softener) containing a fragrance composition according to any one of the items <1> to <16>.

<19> The fabric treatment composition (preferably a softener) according to the item <18>, further containing a quaternary ammonium salt, a germicide, a viscosity modifier, a pH adjuster, and a solvent.

<20> A cosmetic (preferably a perfume, a body cosmetic, or a hair cosmetic) containing a fragrance composition according to any one of the items <1> to <17>.

<21> A cleaner composition (preferably a body cleaner composition (for example, a skin cleaner composition or a hair cleaner composition), a cleaner composition for clothing, or a cleaner composition for hard surfaces (for example, an all purpose cleaner or a cleaner composition for tableware), more preferably a body cleaner composition or a cleaner composition for clothing, and further preferably a cleaner composition for clothing) containing a fragrance composition according to any one of the items <1> to <17>.

<22> A cleaner composition (preferably a powder cleaner composition or a liquid cleaner composition, more preferably a liquid cleaner composition) containing a fragrance composition according to any one of the items <1> to <17>.

<23> A fragrant deodorant containing a fragrance composition according to any one of the items <1> to <17>.

<24> A cleaning nonwoven fabric containing a fragrance composition according to any one of the items <1> to <17>.

<25> A method of producing 3,6-dimethylheptane-2-ol, including a step of obtaining 3,6-dimethylheptane-2-ol by carrying out a cross aldol reaction using isovaleraldehyde and 2-butanone, and then dehydrating and reducing it.

<26> 3,6-dimethylheptane-2-ol.

<27> 7-methyloctane-3-ol.

<28> Use of a fragrance composition according to any one of the items <1> to <17>, as a fragrance component.

<29> A method of using 3,6-dimethylheptane-2-ol as a fragrance component.

EXAMPLES

Details of the measurement methods carried out in the following production examples and the like are described together below.
[Compound Identification]
The structure of each compound obtained in the following production examples and the like was identified by a nuclear magnetic resonance spectrum ($^1$H-NMR, $^{13}$C-NMR). The nuclear magnetic resonance spectrum was measured using chloroform-d as a solvent, by "Mercury 400" (product name) manufactured by Varian.

Production Example 1

Production of 3,6-dimethylhept-3-ene-2-one (Compound (III)) and 7-methyloct-4-en-3-one (Compound (IV))

[Chemical Formula 4]

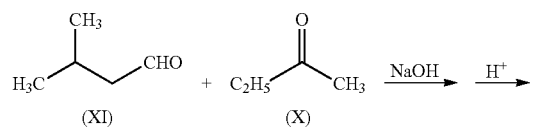

(XI)    (X)

-continued

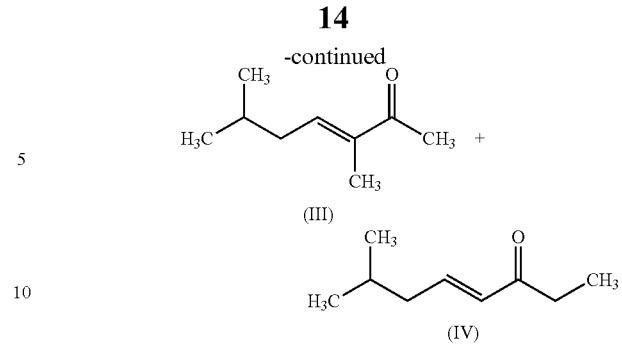

(III)

(IV)

In a flask, sodium hydroxide (0.1 g), water (20 g), and 2-butanone (X) (42 g, 0.58 mole) were placed and maintained at 15° C., and isovaleraldehyde (XI) (20 g, 0.23 mole) was dropped in five hours while stirring. Then sodium hydroxide (0.2 g) was added thereto additionally, which was further stirred at 25° C. for 48 hours. After stirring, the reaction solution was allowed to stand still and then the lower layer was removed. Thereafter, excess 2-butanone (X) was removed from the upper layer by distillation.

Subsequently, 85% phosphoric acid (1 g) was added to the upper layer portion of the reaction solution. With a water fractionator being attached to the flask, it was heated to 120° C. to be dehydrated. Sodium hydroxide (0.7 g) was added to the reaction solution thus dehydrated to neutralize it and then magnesium sulfate was added to dry it. Thereafter, the magnesium sulfate was removed by filtration. The reaction solution thus obtained was concentrated and thereby a residue (21 g) was obtained.

The residue thus obtained was purified using a silica gel column (Eluent: Hexane:Ethyl acetate=99:1 (v/v)). The purified product thus obtained was further purified by distillation, and thereby 11 g of Compound (III) and 2 g of Compound (IV) were obtained.

Compound (III) thus obtained had a purity of 97% and Compound (IV) had a purity of 94%.

Production Example 2

Production of 3,6-dimethylheptane-2-ol (Compound (I))

[Chemical Formula 5]

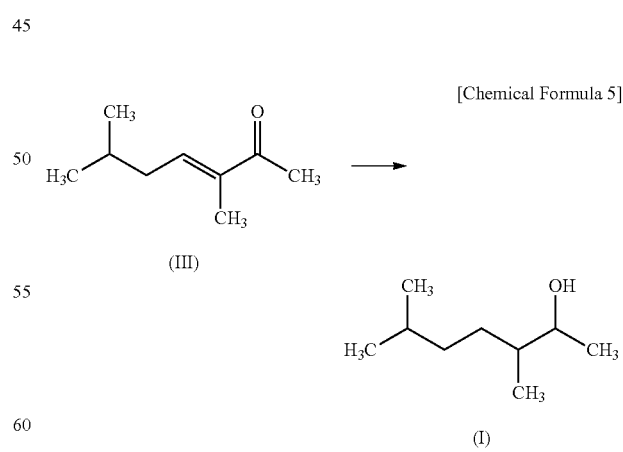

(III)

(I)

In a pressure resistant vessel, 5% active carbon supporting ruthenium catalyst (0.3 g), isopropyl alcohol (2.5 g), and Compound (III) (6 g) obtained in Production Example 1 were placed and then were hydrogenated at 90° C. under a hydrogen pressure of 0.5 MPa for 6.5 hours. The reaction solution thus obtained was filtered and thereby 6 g of filtrate was obtained (with a yield of 95%).

The filtrate thus obtained was concentrated and the concentrated solution thus obtained was purified using a silica gel column (Eluent: Hexane:Ethyl acetate=97:3 (v/v)). The purified product thus obtained was further purified by distillation and thereby 2 g of Compound (I) was obtained. Compound (I) thus obtained had a purity of 100%.

With respect to Compound (I), measurement results of $^1$H-NMR and $^{13}$C-NMR as well as odor evaluation are shown below.

$^1$H-NMR (CDCl$_3$, 400 MHz, δ ppm): 0.85-0.92 (m, 9H), 1.02-1.20 (m, 5H), 1.20-1.36 (m, 2H), 1.36-1.58 (m, 3H), 3.62-3.76 (m, 1H)

$^{13}$C-NMR (CDCl$_3$, 400 MHz, δ ppm): 14.7 (CH$_3$), 15.0 (CH$_3$), 19.7 (CH$_3$), 20.7 (CH$_3$), 22.9 (CH$_3$), 23.3 (CH$_3$), 28.7 (CH$_2$), 30.7 (CH), 30.8 (CH), 37.0 (CH$_2$), 37.0 (CH$_2$), 40.4 (CH), 40.7 (CH), 71.7 (CH), 72.0 (CH).

Odor Evaluation: Floral, Citrus, Slightly Woody

Production Example 3

Production of 7-methyloctane-3-ol (Compound (II))

[Chemical Formula 6]

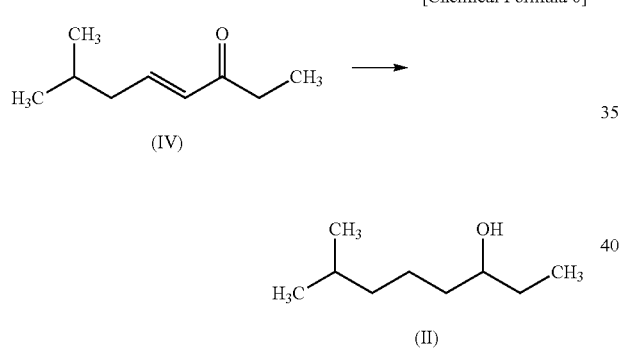

In a pressure resistant vessel, 5% active carbon supporting ruthenium catalyst (0.1 g), isopropyl alcohol (0.6 g), and Compound (IV) (1.5 g) obtained in Production Example 1 were placed and then were hydrogenated at 90° C. under a hydrogen pressure of 0.5 MPa for 22 hours. The reaction solution thus obtained was filtered and thereby 1.4 g of filtrate was obtained (with a yield of 93%).

The filtrate thus obtained was concentrated and the concentrated solution thus obtained was purified using a silica gel column (Eluent: Hexane:Ethyl acetate=97:3 (v/v)). The purified product thus obtained was further purified by distillation and thereby 1 g of Compound (II) was obtained. Compound (II) thus obtained had a purity of 98.8% (with 1.2% of Compound (I)).

With respect to Compound (II), measurement results of $^1$H-NMR and $^{13}$C-NMR as well as odor evaluation are shown below.

$^1$H-NMR (CDCl$_3$, 400 MHz, δ ppm): 0.88 (d, J=6.8 Hz, 6H), 0.94 (t, J=7.2 Hz, 3H), 1.14-1.24 (m, 2H), 1.24-1.60 (m, 8H), 3.48-3.58 (m, 1H)

$^{13}$C-NMR (CDCl$_3$, 400 MHz, δ ppm): 10.4 (CH$_3$), 23.0 (CH$_3$), 23.1 (CH$_3$), 23.9 (CH$_2$), 28.4 (CH), 30.6 (CH$_2$), 37.6 (CH$_2$), 39.4 (CH$_2$), 73.7 (CH).

Odor Evaluation: Fruity Floral, Citrus

Production Example 4

Production of Mixture of Compound (I) and Compound (II)

[Chemical Formula 7]

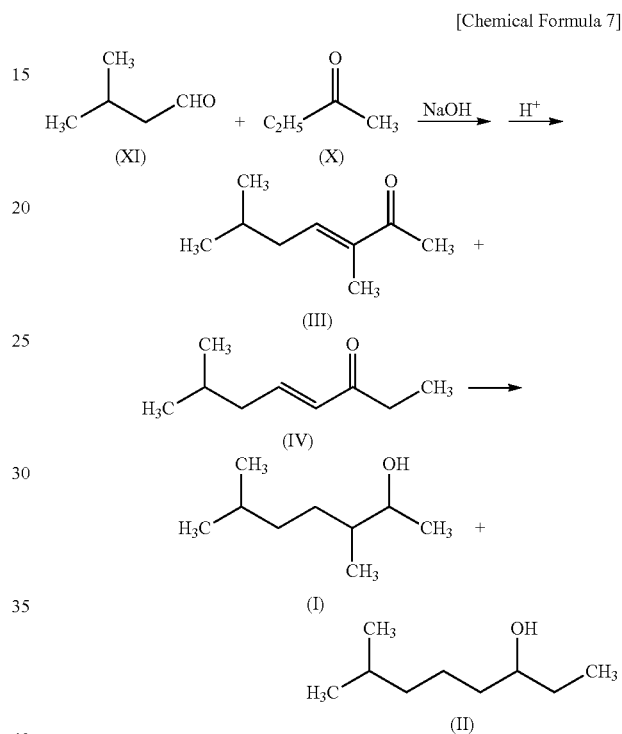

In a flask, sodium hydroxide (2.0 g), water (140 g), and 2-butanone (X) (293 g, 4.1 mole) were placed and isovaleraldehyde (XI) (143 g, 1.7 mole) was dropped at a normal temperature of 26° C. in three hours while stirring. Then sodium hydroxide (1.2 g) was added thereto additionally, which was further stirred at 26° C. for 20 hours. After stirring, the reaction solution was allowed to stand still and then the lower layer was removed. Thereafter, 10.2 g of 6N sulfuric acid aqueous solution was added to the upper layer to neutralize it and then excess 2-butanone (X) was removed.

Subsequently, 85% phosphoric acid (6 g) was added to the upper layer portion of the reaction solution. With a water fractionator being attached to the flask, it was heated to 120° C. under a reduced pressure of 6.7 kPa to be dehydrated. Sodium hydroxide (3.7 g) was added to the reaction solution thus dehydrated to neutralize it and then magnesium sulfate was added to dry it. Thereafter, the magnesium sulfate was removed by filtration. The reaction solution thus obtained was concentrated and thereby a residue (199 g) was obtained.

The residue thus obtained was evaporated to dryness under reduced pressure (up to 130° C./up to 5.0 kPa) and thereby a fraction with a composition in which the weight ratio of Compound (III) and Compound (IV) (Compound (III):Compound (IV)) was 92:8 was obtained. The mass ratio of Compound (III) and Compound (IV) (Compound (III): Compound (IV)) was also 92:8.

In a pressure resistant vessel, 5% active carbon supporting ruthenium catalyst (5.3 g) and the fraction (175 g) thus obtained were placed and then were hydrogenated at 98° C. under a hydrogen pressure of 0.6 MPa for 53 hours. The reaction solution thus obtained was filtered and thereby 174 g of filtrate was obtained (with a yield of 99%).

The filtrate (168 g) thus obtained (the weight ratio of Compound (I) and Compound (II) (Compound (I):Compound (II)) was 91:9, and the mass ratio of Compound a) and Compound an (Compound (I):Compound (II)) was also 91:9) was purified using a 20-step rectifier (the initial rectification; 112° C./2.6 kPa, at a reflux ratio of 20, the main rectification; (112 to 125° C.)/(2.6 to 1.3 kPa), at a reflux ratio of 10 to 5, and the final rectification; 150° C./0.8 kPa, at a reflux ratio of 5). Thus, a fraction (132 g) with a weight ratio of 96:4 (Compound (I):Compound (II)) was obtained. The mass ratio of Compound (I) and Compound (II) (Compound (I):Compound (II)) was also 96:4.

Comparative Production Example 1

Production of 2,5-dimethylhexane-1-ol (Also Referred to as "Compound (XX)" in the Present Description)

[Chemical Formula 8]

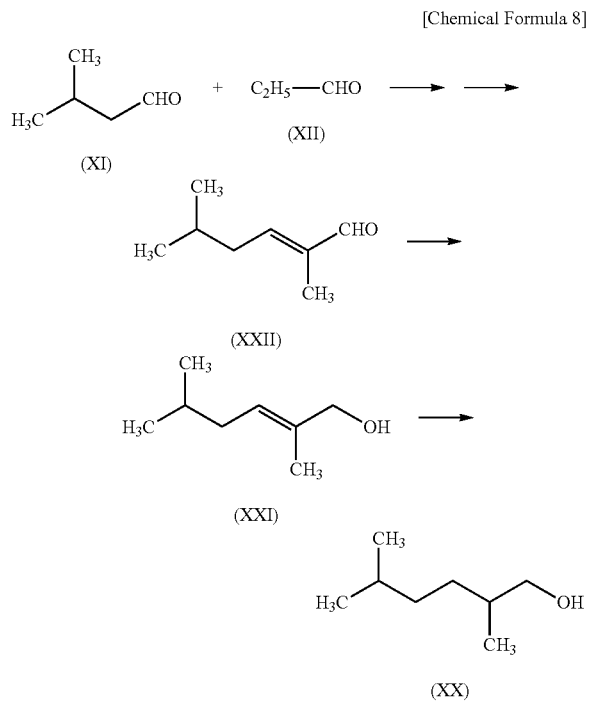

In a flask, piperidine (0.9 g), heptanoic acid (1.4 g), and isovaleraldehyde (XI) (20 g) were placed and propionaldehyde (XII) (10 g) was dropped at 75° C. in three hours while stirring. The reaction solution thus obtained was cooled, which was then separated into layers and the lower layer was removed. Thereafter, acetic acid (1 g) and water (3 g) were added to the upper layer to neutralize it. Magnesium sulfate was added to the upper layer thus obtained to dry it and then the magnesium sulfate was removed by filtration. The reaction solution thus obtained was concentrated and thereby 2,5-dimethylhex-2-enal (referred to as "Compound (XXII)" in the present description) (20 g) was obtained (with the yield of Compound (XXII) being 66%).

In a flask, methanol (20 g), 50% aqueous sodium hydroxide solution (0.2 g), water (8 g), and sodium borohydride (2 g) were placed and Compound (XXII) (20 g) was dropped thereinto at 15° C. in 0.5 hour, which was further stirred for 0.5 hour. Then, 6N sulfuric acid aqueous solution (20 mL) was added to the reaction solution to decompose excess sodium borohydride. Further 50% aqueous sodium hydroxide solution (5 g) was added thereto and thereby the reaction solution was neutralized. Thereafter, methanol was evaporated from the reaction solution at atmospheric pressure and then magnesium sulfate was added to the residual liquid to dry it. Thereafter, the magnesium sulfate was removed by filtration. The residual liquid thus obtained was concentrated and thereby a concentrated solution 14 g was obtained (with the yield of 2,5-dimethylhex-2-ene-1-ol being 81%). The concentrated solution thus obtained was purified by a silica gel column (Eluent: Hexane:Ethyl acetate=97:3 (v/v)) and thereby 2,5-dimethylhex-2-ene-1-ol (referred to as "Compound (XXI)" in the present description) (1.4 g) was obtained. Compound (XXI) thus obtained had a purity of 98%.

In a pressure resistant vessel, 5% active carbon supporting ruthenium catalyst (0.02 g), isopropyl alcohol (1.2 g), and Compound (XXI) (0.3 g) were placed and then were hydrogenated at 90° C. under a hydrogen pressure of 0.5 MPa for three hours. The reaction solution thus obtained was filtered and thereby a filtrate (0.3 g) was obtained (with a yield of 88%).

The filtrate thus obtained was concentrated and the concentrated solution thus obtained was purified by distillation. Thus, 0.1 g of 2,5-dimethylhexane-1-ol (XX) was obtained. Compound (XX) thus obtained had a purity of 100%.

With respect to Compound (XX), measurement results of $^1$H-NMR and odor evaluation are shown below.

$^1$H-NMR (CDCl$_3$, 400 MHz, δ ppm): 0.88 (d, J=6.4 Hz, 3H), 0.88 (d, J=6.4 Hz, 3H), 0.92 (d, J=6.4 Hz, 3H), 1.02-1.30 (m, 4H), 1.32-1.64 (m, 3H), 3.38-3.54 (m, 2H).

Odor Evaluation: Herbal, Woody, Citrus

Comparative Production Example 2

Production of 2,5-dimethyl-2-ethylhexane-1-ol (Also Referred to as "Compound (XXV)" in the Present Description)

[Chemical Formula 9]

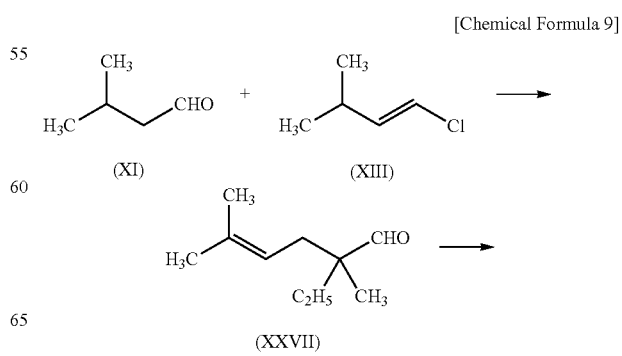

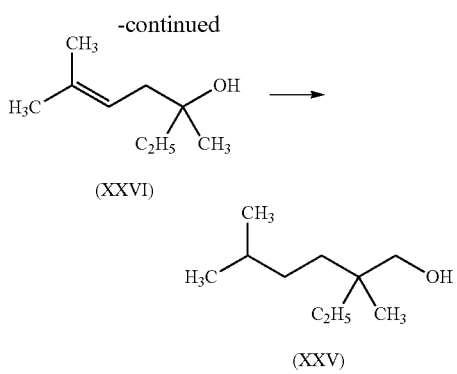

(XXVI)

(XXV)

In a flask, toluene (20 mL), sodium hydroxide (10 g), butylammonium iodide (TBAI) (1.3 g), and water (10 mL) were added and 2-methylbutanal (XI) (21 g) and 1-chloro-3-methyl-2-butene (XIII) (31 g) were dropped at 70° C. in one hour. Thereafter, this was separated into layers using water and ether. The upper layer (an organic layer) was washed with an aqueous sodium sulfite solution and then magnesium sulfate was added thereto to dry it. Thereafter, the magnesium sulfate was removed by filtration. The organic layer thus obtained was concentrated and thereby 2-ethyl-2,5-dimethylhexyl-4-enal (also referred to as Compound (XXVII) in the present description) (42 g) was obtained.

In a flask, methanol (5 g), 50% aqueous sodium hydroxide solution (1 g), water (1 g), and sodium borohydride (0.5 g) were placed and Compound (XXVII) (5 g) was dropped thereinto at 15° C. in 0.5 hour, which was then stirred for one hour. Then, 6N sulfuric acid aqueous solution was added to the reaction solution thus obtained to decompose excess sodium borohydride. Further 50% aqueous sodium hydroxide solution was added thereto and thereby the reaction solution was neutralized. Thereafter, methanol was evaporated from the reaction solution at atmospheric pressure. Magnesium sulfate was added to the residual liquid thus obtained to dry it and then the magnesium sulfate was removed by filtration. The residual liquid thus obtained was concentrated and thereby a concentrated solution 3.8 g was obtained (with the yield of 2-ethyl-2,5-dimethylhex-4-ene-1-ol being 63%). The concentrated solution thus obtained was purified by a silica gel column (Eluent: Hexane:Ethyl acetate=97:3 (v/v)) and thereby 2-ethyl-2,5-dimethylhex-4-ene-1-ol (referred to as "Compound (XXVI)" in the present description) (2 g) was obtained. Compound (XXVI) had a purity of 100%.

In a pressure resistant vessel, 5% active carbon supporting ruthenium catalyst (0.03 g), isopropyl alcohol (1.2 g), and Compound (XXVI) (0.5 g) were placed and then were hydrogenated at 90° C. under a hydrogen pressure of 0.5 MPa for 2.5 hours. The reaction solution thus obtained was filtered and thereby a filtrate (0.83 g) was obtained (with a yield of 99%).

The filtrate thus obtained was concentrated and the concentrated solution thus obtained was purified by distillation. Thus, 0.5 g of Compound (XXV) was obtained. Compound (XXV) thus obtained had a purity of 100%.

With respect to Compound (XXV), measurement results of $^1$H-NMR and odor evaluation are shown below.

$^1$H-NMR (CDCl$_3$, 400 MHz, δ ppm): 0.81 (t, J=7.6 Hz, 3H), 0.81 (s, 3H), 0.89 (d, J=6.8 Hz, 6H), 1.05-1.35 (m, 6H), 1.35-1.50 (m, 1H), 3.34 (d, J=6.0 Hz, 2H).

Odor Evaluation: Woody, Herbal, Citrus

Examples 1 to 6 and Comparative Examples 1 to 3

Compound (I) obtained in Production Example 2 and Compound (II) obtained in Production Example 3 were used to prepare fragrance compositions, each of which had the composition shown in Table 1. In Table 1, numerical values are indicated by part by mass (they are the same values even when being indicated by part by weight. The same applies to the following.). Furthermore, as comparative examples, fragrance compositions, each of which had the composition shown in Table 1, were produced using Compound (XX) obtained in Comparative Production Example 1, Compound (XXV) obtained in Comparative Production Example 2, and 3,4,5,6,6-pentamethylheptane-2-ol (Kohinol (product name), manufactured by IFF) (also referred to as "Compound (XXX)" in the present description) represented by Formula (XXX) below.

[Chemical Formula 10]

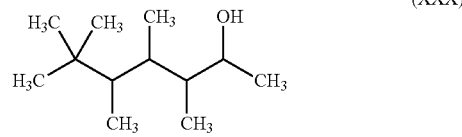

(XXX)

[Odor Evaluation]

One expert, who had an experience of seven years of perfume formulation and fragrance evaluation, determined the fragrance note by a smelling strip method. About 5 mm of the end of each smelling strip (fragrance test paper with a width of 6 mm and a length of 150 mm) was immersed in a sample and thereby evaluation was performed.

With respect to the odor, fragrances that are sensed mainly (main odors) were listed and further fragrances that are sensed secondarily (secondary odors) were also listed. Furthermore, the presence or absence of a floral feeling was also determined.

TABLE 1

| Fragrance Materials | Examples | | | | | Comparative Examples | | |
|---|---|---|---|---|---|---|---|---|
| | 1 | 2 | 3 | 4 | 5 | 1 | 2 | 3 |
| Compound (I) | 100 | 94 | 90.3 | 83.2 | 82.8 | — | — | — |
| Compound (II) | — | 6 | 9.7 | 16.8 | 17.2 | — | — | — |
| Compound (XX) | — | — | — | — | — | 100 | — | — |
| Compound (XXV) | — | — | — | — | — | — | 100 | — |
| Compound (XXX) | — | — | — | — | — | — | — | 100 |

TABLE 1-continued

| Fragrance Materials | Examples | | | | | Comparative Examples | | |
|---|---|---|---|---|---|---|---|---|
| | 1 | 2 | 3 | 4 | 5 | 1 | 2 | 3 |
| Presence or Absence of Floral Feeling | Present | Present | Present | Present | Present | Absent | Absent | Absent |
| Main Odor | Floral | Floral | Floral | Floral | Floral | Herbal | Herbal | Herbal |
| Secondary Odor | Citrus | Citrus | Citrus | Citrus | Citrus | Woody | Herbal | Amber |
| | Woody | Fruity | Fruity | Fruity | Fruity | Citrus | Citrus | — |

As shown in Table 1 above, it was confirmed that the fragrance compositions of the present invention each had a main odor with a floral tone.

Examples 6 to 10

Softeners

Compound (I) obtained in Production Example 2 and Compound (II) obtained in Production Example 3 were used to prepare softeners, each of which had the composition shown in Table 2, and odor evaluation was performed.

[Odor Evaluation]

One expert who had an experience of seven years of blending odors and evaluating fragrances evaluated odors in the following manner. In a 100 ml glass bottle, 50 ml of each of the softeners, which each had the composition shown in Table 2, was placed, which was then sealed and allowed to stand at 25° C. for 24 hours. Thereafter, the expert evaluated the odor at the mouth of the bottle when it was opened.

With respect to the odor, fragrances that were sensed mainly (main odors) were listed sequentially from the strongest, and the assessment was also noted.

As shown in Table 2 above, it was confirmed that the softeners containing the fragrance compositions of the present invention allowed a strong floral feeling to be obtained.

Examples 11 to 13 and Comparative Examples 4 to 7

Fragrance Compositions for Perfumes

Compound (I) obtained in Production Example 2 and Compound (II) obtained in Production Example 3 were used to prepare fragrance compositions for perfumes, each of which had the composition shown in Table 3. Furthermore, Compound (XX) obtained in Comparative Production Example 1, Compound (XXV) obtained in Comparative Production Example 2, and Compound (XXX) were used to produce fragrance compositions for perfumes, each of which had the composition shown in Table 3, as comparative examples. Odor evaluation was carried out by the same method as in Example 1 and the odors obtained when the compositions were used for perfumes were assessed by sensory evaluation. The results of the sensory evaluation are shown in Table 4.

TABLE 2

| | | Examples | | | | |
|---|---|---|---|---|---|---|
| | | 6 | 7 | 8 | 9 | 10 |
| Softener | N,N-di[2-(alkanoyloxy)ethyl]-N-(2-hydroxyethyl)-N-methyl ammonium sulfate | 15 | 15 | 15 | 15 | 15 |
| | Stearic acid | 0.5 | 0.5 | 0.5 | 0.5 | 0.5 |
| | Calcium chloride | 0.05 | 0.05 | 0.05 | 0.05 | 0.05 |
| | Ethanol | 2 | 2 | 2 | 2 | 2 |
| | Fragrance composition | 0.2 | 0.2 | 0.2 | 0.2 | 0.2 |
| | Ion exchanged water | Suitable amount | Suitable amount | Suitable amount | Suitable amount | Suitable amount |
| | pH Adjuster | Suitable amount | Suitable amount | Suitable amount | Suitable amount | Suitable amount |
| | Total % by mass | 100 | 100 | 100 | 100 | 100 |
| | pH | 4 | 4 | 4 | 4 | 4 |
| Composition of Fragrance Composition | Compound (I) | 100 | 94 | 90.3 | 83.2 | 82.8 |
| | Compound (II) | — | 6 | 9.7 | 16.8 | 17.2 |
| Evaluation | Main Odor | Floral | Floral | Floral | Floral | Floral |
| | | Citrus | Citrus | Citrus | Fruity | Citrus |
| | | — | Fruity | Fruity | Citrus | — |
| | Assessment | Excellent fresh feeling | Excellent fresh feeling | Excellent fresh feeling | Good fresh feeling | Good fresh feeling |

TABLE 3

|  | C. Example 4 | Examples 11 | 12 | 13 | C. Examples 5 | 6 | 7 |
|---|---|---|---|---|---|---|---|
| cis-3-Hexenol | 2 | 2 | 2 | 2 | 2 | 2 | 2 |
| cis-3-Hexenyl salicylate | 50 | 50 | 50 | 50 | 50 | 50 | 50 |
| Liffarome[1] | 2 | 2 | 2 | 2 | 2 | 2 | 2 |
| Styralyl acetate | 10 | 10 | 10 | 10 | 10 | 10 | 10 |
| Calone[2] | 0.5 | 0.5 | 0.5 | 0.5 | 0.5 | 0.5 | 0.5 |
| Floralozone[3] | 5 | 5 | 5 | 5 | 5 | 5 | 5 |
| Helional[4] | 50 | 50 | 50 | 50 | 50 | 50 | 50 |
| Damascenone | 1 | 1 | 1 | 1 | 1 | 1 | 1 |
| Geraniol | 50 | 50 | 50 | 50 | 50 | 50 | 50 |
| Phenyl hexanol | 20 | 20 | 20 | 20 | 20 | 20 | 20 |
| Benzyl acetate | 50 | 50 | 50 | 50 | 50 | 50 | 50 |
| Methyl dihydrojasmonate | 200 | 200 | 200 | 200 | 200 | 200 | 200 |
| Bourgeonal[5] | 10 | 10 | 10 | 10 | 10 | 10 | 10 |
| Ethyllinalool | 70 | 70 | 70 | 70 | 70 | 70 | 70 |
| Lilial[6] | 100 | 100 | 100 | 100 | 100 | 100 | 100 |
| α-Terpineol | 50 | 50 | 50 | 50 | 50 | 50 | 50 |
| β-Ionone | 5 | 5 | 5 | 5 | 5 | 5 | 5 |
| Amber Core[7] | 50 | 50 | 50 | 50 | 50 | 50 | 50 |
| Sandalmysore Core[8] | 5 | 5 | 5 | 5 | 5 | 5 | 5 |
| Methyl atrarate | 2 | 2 | 2 | 2 | 2 | 2 | 2 |
| Ambrettolide | 2 | 2 | 2 | 2 | 2 | 2 | 2 |
| Muscone | 2 | 2 | 2 | 2 | 2 | 2 | 2 |
| Compound (I) | — | 50 | 45.2 | 41.4 | — | — | — |
| Compound (II) | — | — | 4.8 | 8.6 | — | — | — |
| Compound (XX) | — | — | — | — | 50 | — | — |
| Compound (XXV) | — | — | — | — | — | 50 | — |
| Compund (XXX) | — | — | — | — | — | — | 50 |
| Dipropylene glycol | 263.5 | 213.5 | 213.5 | 213.5 | 213.5 | 213.5 | 213.5 |

[1]Liffarome: IFF (Trade Name), Compound Name: cis-3-hexenyl methyl carbonate,
[2]Calone: Firmenich (Trade Name), Compound Name: 7-methyl-3,5-dihydro-2H-benzo-dioxepin-3-one),
[3]Floralozone: IFF (Trade Name), Compound Name: p-ethyl-α,α-dimethylhydrocinnamaldehyde),
[4]Helional: IFF (Trade Name), Compound Name: α-methyl-3,4-methylenedioxyhydrocinnamaldehyde),
[5]Bourgeonal: Givaudan (Trade Name), Compound Name: 3-(p-tert-butylphenyl)-propanal),
[6]Lilial: Givaudan (Trade Name), Compound Name: p-tert-butyl-α-methylhydrocinnamaldehyde,
[7]Amber Core: Kao Corporation (Trade Name), Compound Name: 1-(2-tert-butyl cyclohexyloxy)-2-butanol,
[8]Sandalmysore Core: Kao Corporation (Trade Name), Compound Name: 2-methyl-4-(2,2,3-trimethyl-3-cyclopenten-1-yl)-2-buten-1-ol

TABLE 4

| | |
|---|---|
| C. Example 4 | A fresh and sweet aquatic-floral like odor |
| Example 11 | Brightness reminding of rose and muguet was added, which resulted in a soft and harmonious odor. |
| Example 12 | Brightness reminding of rose and muguet was added, which resulted in a soft and harmonious odor. |
| Example 13 | Brightness reminding of rose and muguet was added, which resulted in a soft and harmonious odor. |
| C. Example 5 | Herbal-like grassy-smelling was added, and there was no difference in floral feeling from the blank (Comparative Example 4). |
| C. Example 6 | Woody-like bitterness was added, and there was no difference in floral feeling from the blank (Comparative Example 4). |
| C. Example 4 | Woody-like bitterness was added, and there was no difference in floral feeling from the blank (Comparative Example 4). |

As shown in Table 4 above, it was confirmed that the fragrance compositions of the present invention were able to obtain rose and muguet tones by containing additional fragrance components.

Examples 14 to 16 and Comparative Examples 8 to 11

Fragrance Compositions for Liquid Detergents for Clothing

Compound (I) obtained in Production Example 2 and Compound (II) obtained in Production Example 3 were used to prepare white floral-type fragrance compositions for liquid detergents for clothing, each of which had the composition shown in Table 5. Furthermore, Compound (XX) obtained in Comparative Production Example 1, Compound (XXV) obtained in Comparative Production Example 2, and Compound (XXX) were used to produce white floral-type fragrance compositions for liquid detergents for clothing, each of which had the composition shown in Table 5, as comparative examples. Odor evaluation was carried out by the same method as in Example 1 and the odors obtained when the compositions were used for detergents were assessed by sensory evaluation. The results of the sensory evaluation are shown in Table 6.

TABLE 5

|  | C. Ex. 8 | Examples 14 | 15 | 16 | C. Examples 9 | 10 | 11 |
|---|---|---|---|---|---|---|---|
| Dihydromyrcenol | 50 | 50 | 50 | 50 | 50 | 50 | 50 |
| Triplal[1] | 4 | 4 | 4 | 4 | 4 | 4 | 4 |
| Magnol[2] | 2 | 2 | 2 | 2 | 2 | 2 | 2 |
| Undecavertol[3] | 2 | 2 | 2 | 2 | 2 | 2 | 2 |
| o-t-Butyl cyclohexyl acetate | 20 | 20 | 20 | 20 | 20 | 20 | 20 |
| Poirenate[4] | 2 | 2 | 2 | 2 | 2 | 2 | 2 |
| Raspberry ketone | 5 | 5 | 5 | 5 | 5 | 5 | 5 |
| Fruitate[5] | 2 | 2 | 2 | 2 | 2 | 2 | 2 |
| Tricyclodecenyl propionate | 100 | 100 | 100 | 100 | 100 | 100 | 100 |
| Geraniol | 100 | 100 | 100 | 100 | 100 | 100 | 100 |
| Rose oxide | 1 | 1 | 1 | 1 | 1 | 1 | 1 |
| α-Hexyl cinnamaldehyde | 100 | 100 | 100 | 100 | 100 | 100 | 100 |
| Methyl dihydrojasmonate | 50 | 50 | 50 | 50 | 50 | 50 | 50 |
| Dimethyl anthranilate | 5 | 5 | 5 | 5 | 5 | 5 | 5 |
| Methyl-b-naphthyl ketone | 5 | 5 | 5 | 5 | 5 | 5 | 5 |
| Lilial[6] | 100 | 100 | 100 | 100 | 100 | 100 | 100 |
| Linalool | 50 | 50 | 50 | 50 | 50 | 50 | 50 |
| Terpineol | 50 | 50 | 50 | 50 | 50 | 50 | 50 |
| Phenylacetaldehyde dimethyl acetal | 4 | 4 | 4 | 4 | 4 | 4 | 4 |
| Amber Core[7] | 30 | 30 | 30 | 30 | 30 | 30 | 30 |
| Isobornylcyclohexanol | 20 | 20 | 20 | 20 | 20 | 20 | 20 |
| Galaxolide50% IPM[8] | 60 | 60 | 60 | 60 | 60 | 60 | 60 |
| Ambroxan[9] 5% DPG[10] | 4 | 4 | 4 | 4 | 4 | 4 | 4 |
| Heliotropyl acetone | 1 | 1 | 1 | 1 | 1 | 1 | 1 |
| Compound (I) | — | 50 | 45.2 | 41.4 | — | — | — |
| Compound (II) | — | — | 4.8 | 8.6 | — | — | — |
| Compound (XX) | — | — | — | — | 50 | — | — |

TABLE 5-continued

|  | C. Ex. 8 | Examples | | | C. Examples | | |
|---|---|---|---|---|---|---|---|
|  |  | 14 | 15 | 16 | 9 | 10 | 11 |
| Compound (XXV) | — | — | — | — | — | 50 | — |
| Compound (XXX) | — | — | — | — | — | — | 50 |
| Dipropylene glycol | 233 | 183 | 183 | 183 | 183 | 183 | 183 |

[1] Triplal: IFF (Trade Name), Compound Name: 2,4-dimethyl-3-cyclohexene-1-carboxaldehyde,
[2] Magnol: Kao Corporation (Trade Name), a mixture containing ethyl norbornyl cyclohexanol as a main component,
[3] Undecavertol: Givaudan Roure K.K. (Trade Name), Compound Name: 4-methyl-3-decene-5-ol
[4] Poirenate: Kao Corporation (Trade Name), Compound Name: ethyl 2-cyclohexyl propionate,
[5] Fruitate: Kao Corporation (Trade Name), Compound Name: ethyl tricyclo [$5.2.1.0^{2.6}$] decan-2-carboxylate),
[6] Lilial: Givaudan (Trade Name), Compound Name: p-tert-butyl-α-methylhydrocinnamaldehyde,
[7] Amber Core: Kao Corporation (Trade Name), Compound Name: 1-(2-tert-butyl cyclohexyloxy)-2-butanol,
[8] 50% IPM: indicating a 50% isopropyl myristate (IPM) solution.
[9] Ambroxan: Kao Corporation (Trade Name), Compound Name: [3aR-(3aα,5aβ,9aα,9bβ)] dodecahydro-3a,6,6,9a-tetramethyl naphto[2,1-b]furan,
[10] DPG: Dipropylene glycol.

TABLE 6

| C. Example 8 | A bright white floral-like odor |
| Example 14 | A fresh feeling and softness were added to brightness. |
| Example 15 | A fresh feeling and softness were added to brightness. |
| Example 16 | A fresh feeling and softness were added to brightness. |
| C. Example 9 | A floral feeling was weak and there was no difference from the blank (Comparative Example 8). |
| C. Example 10 | A floral feeling was weak and there was no difference from the blank (Comparative Example 8). |
| C. Example 11 | A floral feeling was weak and there was no difference from the blank (Comparative Example 8). |

As shown in Table 6 above, it was confirmed that fragrance compositions for liquid detergents for clothing of the present invention were able to obtain a strong floral tone.

0.5 part by mass of the fragrance composition of Example 14 shown in Table 5 was blended into 99.5 parts by mass of a liquid detergent composition having the composition shown in Table 7 and thereby a liquid detergent composition for clothing was obtained. 20 g of this composition was weighed and then was dissolved in 30 L of water. A cotton towel (2 kg) was placed in this water solution and then was laundered for five minutes, was rinsed for one minute, and thereafter was spin-dried. The odor of this cotton towel was evaluated. In the same manner, with respect to Examples 15 and 16 and Comparative Examples 8 to 11, odors obtained after spin-dry were evaluated. The results of the sensory evaluation are shown in Table 8.

TABLE 7

| Ingredients | % by mass |
|---|---|
| Alkyl($C_{12}$-$C_{14}$)O(EO)$_7$(PO)$_2$(EO)$_3$H | 35 |
| Sodium linear alkyl($C_{10}$-$C_{18}$) benzenesulfonate | 1 |
| Fatty acid (lauric acid and myristic acid) | 1 |
| Monoethanolamine | 5 |
| Sodium sulfite | 0.1 |
| Ethanol | 2 |
| Enzyme | 0.5 |
| Water | Balance |
| Total | 99.5 |

TABLE 8

| C. Example 8 | A bright floral odor |
| Example 14 | A natural floral odor with increased freshness |
| Example 15 | A natural floral odor with increased freshness |
| Example 16 | A natural floral odor with increased freshness |
| C. Example 9 | A floral feeling was weak and there was no difference from the blank (Comparative Example 8). |
| C. Example 10 | A floral feeling was weak and there was no difference from the blank (Comparative Example 8). |
| C. Example 11 | A floral feeling was weak and there was no difference from the blank (Comparative Example 8). |

As shown in Table 8 above, it was confirmed that the fragrance compositions of the present invention had a high diffusibility, which resulted in freshness, and thereby provided a natural floral odor with a feeling of cleanliness.

Examples 17 to 20 and Comparative Example 12

Fragrance Compositions for Powder Detergents for Clothing

Compound (I) obtained in Production Example 2 and Compound (II) obtained in Production Example 3 were used to prepare floral-type fragrance compositions for powder detergents for clothing, each of which had the composition shown in Table 9. Odor evaluation was carried out by the same method as in Example 1 and the odors obtained when the compositions were used for powder detergents for clothing were assessed by sensory evaluation. The results of the sensory evaluation are shown in Table 10.

TABLE 9

|  | C. Ex. 12 | Examples | | | | C. Ex. 13 |
|---|---|---|---|---|---|---|
|  |  | 17 | 18 | 19 | 20 |  |
| Orange oil | 100 | 100 | 100 | 100 | 100 | 100 |
| Linalool | 100 | 100 | 100 | 100 | 100 | 100 |
| γ-Methyl ionone | 100 | 100 | 100 | 100 | 100 | 100 |
| Lilial | 100 | 100 | 100 | 100 | 100 | 100 |
| Phenylethyl alcohol | 100 | 100 | 100 | 100 | 100 | 100 |
| Acetyl cedrene | 60 | 60 | 60 | 60 | 60 | 60 |
| Dihydromyrcenol | 40 | 40 | 40 | 40 | 40 | 40 |
| Anisaldehyde | 50 | 50 | 50 | 50 | 50 | 50 |
| Benzyl acetate | 50 | 50 | 50 | 50 | 50 | 50 |
| α-Hexyl cinnamaldehyde | 50 | 50 | 50 | 50 | 50 | 50 |
| Amber Core | 40 | 40 | 40 | 40 | 40 | 40 |
| Methyl-β-naphthyl ketone | 30 | 30 | 30 | 30 | 30 | 30 |
| Terpineol | 20 | 20 | 20 | 20 | 20 | 20 |
| Citronellol | 20 | 20 | 20 | 20 | 20 | 20 |
| Cyclopentadecanolide | 20 | 20 | 20 | 20 | 20 | 20 |
| Sandalmysore Core[11] | 10 | 10 | 10 | 10 | 10 | 10 |
| γ-Undecalactone | 5 | 5 | 5 | 5 | 5 | 5 |
| Ambroxan | 5 | 5 | 5 | 5 | 5 | 5 |
| Compound (I) | — | 96 | 85 | 80 | 70 | — |
| Compound (II) | — | 4 | 15 | 20 | 30 | — |
| Tetrahydrogaraniol | — | — | — | — | — | 100 |
| Dipropylene glycol | — | — | — | — | — | 100 |
| Total | 1000 | 1000 | 1000 | 1000 | 1000 | 1000 |

[11] Sandalmysore Core: Kao Corporation (Trade Name), Compound Name: 2-methyl-4-(2,2,3-trimethyl-3-cyclopenten-1-yl)-2-buten-1-ol

TABLE 10

| | |
|---|---|
| C. Example 12 | A floral like odor with a feeling of cleanliness |
| Example 17 | A fresh odor with an increased feeling of cleanliness |
| Example 18 | A fresh odor with an increased feeling of cleanliness |
| Example 19 | A fresh odor with an increased feeling of cleanliness |
| Example 20 | A fresh odor with an increased feeling of cleanliness, also with slight sweetness |

As shown in Table 10 above, it was confirmed that the fragrance compositions of the present invention provided a feeling of cleanliness by increasing the fresh feeling.

0.4 part by mass of the fragrance composition of Example 17 shown in Table 7 was blended into 99.6 parts by mass of the powder detergent composition having the composition shown in Table 11 and thereby a powder detergent composition for clothing was obtained. 20 g of this composition was weighed and then was dissolved in 30 L of water. A cotton towel (2 kg) was placed in this water solution and then was laundered for five minutes, was rinsed for one minute, and thereafter was spin-dried. The odor of this cotton towel was evaluated. In the same manner, with respect to Examples 18 to 20 and Comparative Example 12, odors obtained after spin-thy were evaluated. The results of the sensory evaluation are shown in Table 12.

TABLE 11

| Ingredients | % by mass |
|---|---|
| Sodium linear alkyl($C_{10}$-$C_{18}$) benzenesulfonate | 30 |
| Sodium alkyl($C_{12}$-$C_{16}$) sulfate | 5 |
| Polyoxyethylene (with an average addition mole number of 6 to 15) alkyl($C_{12}$-$C_{18}$) ether | 10 |
| Soap($C_{14}$-$C_{20}$) | 5 |
| Crystalline aluminosilicate | 25 |
| Sodium carbonate | 15.6 |
| Sodium sulfate | 6 |
| Polyethylene glycol (with a molecular weight of 8,000 to 10,000) | 2 |
| Enzyme granule | 1 |
| Total | 99.6 |

TABLE 12

| | |
|---|---|
| C. Example 12 | A floral odor with a slight woody-amber feeling |
| Example 17 | As compared to Comparative Example 12, a fresh odor with a feeling of cleanliness was added. |
| Example 18 | As compared to Comparative Example 12, a fresh odor with a feeling of cleanliness was added. |
| Example 19 | As compared to Comparative Example 12, a fresh odor with a feeling of cleanliness was added. |
| Example 20 | As compared to Comparative Example 12, a fresh odor with a feeling of cleanliness was added. |

As shown in Table 12 above, it was confirmed that the fragrance compositions of the present invention had an effect of providing a fresh odor with a feeling of cleanliness.

Comparative Example 13

Fragrance Composition for Powder Detergent for Clothing

As a comparative example, tetrahydrogeraniol was used instead of Compound (I) and Compound (II) to produce a floral-type fragrance composition for a liquid detergent for clothing, which had the composition shown in Table 9. Odor evaluation was carried out by the same method as in Example 1 and the odor obtained when the composition was used for a liquid detergent for clothing was assessed by sensory evaluation. As a result, it was confirmed that when tetrahydrogeraniol, which is saturated alcohol, was blended, rose-like softness was provided, but on the other hand, no fresh odor was perceived, and an oil-like odor was provided, which rather resulted in a reduction in feeling of cleanliness.

Furthermore, 0.4 part by mass of the fragrance composition of Comparative Example 13 shown in Table 9 was blended into 99.6 parts by mass of the powder detergent composition having the composition shown in Table 11 and thereby a powder detergent composition for clothing was obtained. 20 g of this composition was weighed and then was dissolved in 30 L of water. A cotton towel (2 kg) was placed in this water solution and then was laundered for five minutes, was rinsed for one minute, and thereafter was spin-dried. The odor of this cotton towel was evaluated. When tetrahydrogeraniol was blended into the fragrance composition, it was found that the spin-dried cotton towel had an odor with a floral feeling, but the feeling of cleanliness was not enhanced as compared to Example 17. Therefore, tetrahydrogeraniol, saturated alcohol, cannot provide a fresh odor effect.

Examples 21 to 22 and Comparative Example 14

Floral-Herbal-Type Fragrance Compositions

Compound (I) obtained in Production Example 2 and Compound (II) obtained in Production Example 3 were used to prepare floral-herbal-type fragrance compositions, each of which had the composition shown in Table 13. Odor evaluation was carried out by the same method as in Example 1 and the results of the sensory evaluation are shown in Table 14.

TABLE 13

| | C. Example | Examples | |
|---|---|---|---|
| | 14 | 21 | 22 |
| Romilat[12] | 350 | 350 | 350 |
| Herbavert[13] | 100 | 100 | 100 |
| Trimethylhexanol | 120 | 120 | 120 |
| Melusat[14] | 100 | 100 | 100 |
| L-menthol | 50 | 50 | 50 |
| γ-methyl ionone | 30 | 30 | 30 |
| α-pinene | 10 | 10 | 10 |
| Isoamyl n-butyrate | 5 | 5 | 5 |
| 2-Methyl butyl 2-methyl butyrate | 5 | 5 | 5 |
| Allyl hexanoate | 2 | 2 | 2 |
| Coumarin | 1 | 1 | 1 |
| Damascenone | 1 | 1 | 1 |
| cis-3-Hexenyl acetate | 1 | 1 | 1 |
| Methyl atrarate | 0.5 | 0.5 | 0.5 |
| Compound (I) | — | 190 | 160 |
| Compound (II) | — | 10 | 40 |
| Dipropylene glycol | 224.5 | 24.5 | 24.5 |
| Total | 1000 | 1000 | 1000 |

[12]Romilat: Kao Corporation (Trade Name), Compound Name: 3-Methyl-3-butenyl 2,2-dimethyl propionate
[13]Herbavert: Kao Corporation (Trade Name), Compound Name: 3,3,5-Trimethylcyclohexyl ethyl ether
[14]Melusat: Kao Corporation (Trade Name), Compound Name: Ethyl 3,5,5-trimethyl hexanoate

TABLE 14

| | |
|---|---|
| C. Example 14 | A refreshing herbal-floral odor |
| Example 21 | Imparting a natural floral feeling that reminds of chamomile |
| Example 22 | Imparting a natural floral feeling that reminds of chamomile |

As shown in Table 14 above, it was confirmed that the fragrance compositions of the present invention provided a natural floral odor.

0.5 part by mass of the fragrance composition of Example 21 shown in Table 13 was blended into 99.5 parts by mass of a house cleaner composition (pH 8.0) that has the composition shown in Table 15 and that is used for floors, furniture, electric appliances, etc. The odor thereof was evaluated at the mouth of the bottle. As a result, a natural herbal-floral odor with a diffusive and fresh feeling of cleanliness was perceived. Furthermore, a suitable amount of this house cleaner composition was allowed to soak into a nonwoven fabric and thereby a cleaning nonwoven fabric was prepared. The odor perceived when a floor was wiped therewith was evaluated. As a result, a diffusive and refreshing odor was perceived.

TABLE 15

| Ingredients | % by mass |
|---|---|
| Nonionic surfactant (dodecylglucoside) | 0.5 |
| Silicone powder | 3.0 |
| Dimethyl polysiloxane | 0.5 |
| n-Paraffin | 2.0 |
| Xanthan gum | 0.08 |
| Ethanol | 20.0 |
| Ion exchanged water | Balance |
| Total | 99.5 |

Furthermore, 0.2 part by mass of the fragrance composition of Example 22 shown in Table 13 was blended into 99.8 parts by mass of a cleaner composition for hard surfaces that is used for toilet and bathroom, which had the composition shown in Table 16. The odor thereof was evaluated at the mouth of the bottle. As a result, a herbal-floral odor with a diffusive fresh feeling of cleanliness was perceived.

TABLE 16

| Ingredients | % by mass |
|---|---|
| Sodium linear alky($C_{10}$-$C_{18}$) benzenesulfonate | 3 |
| Polyoxyethylene (with an average addition mole number of 6 to 15) alkyl($C_{12}$-$C_{18}$) ether | 1 |
| Decyl trimethyl ammonium chloride | 0.5 |
| Propylene glycol monobutyl ether | 5 |
| EDTA | 2 |
| Citric acid | 2 |
| Water | Balance |
| Total | 99.8 |

Examples 23 and 24 and Comparative Example 15

Citrus-Type Fragrance Compositions

Compound (I) obtained in Production Example 2 and Compound (II) obtained in Production Example 3 were used to prepare citrus-type fragrance compositions, each of which had the composition shown in Table 17. Odor evaluation was carried out by the same method as in Example 1 and the results of the sensory evaluation are shown in Table 18.

TABLE 17

| | C. Example | Examples | |
|---|---|---|---|
| | 15 | 23 | 24 |
| Orange oil | 450 | 450 | 450 |
| d-Limonene | 258 | 258 | 258 |
| Lemon oil | 60 | 60 | 60 |
| Grapefruit oil | 40 | 40 | 40 |
| Citronellol | 30 | 30 | 30 |
| Citral | 30 | 30 | 30 |
| Geraniol | 30 | 30 | 30 |
| n-Decanal | 5 | 5 | 5 |
| Ethyl 2-methyl butyrate | 15 | 15 | 15 |
| n-Octanal | 2 | 2 | 2 |
| Styralyl acetate | 30 | 30 | 30 |
| Compound (I) | — | 48 | 40 |
| Compound (II) | — | 2 | 10 |
| Isopropyl myristate | 50 | — | — |
| Total | 1000 | 1000 | 1000 |

TABLE 18

| | |
|---|---|
| C. Example 15 | A citrus odor |
| Example 23 | A fresh and juicy citrus odor |
| Example 24 | A fresh and juicy citrus odor |

As shown in Table 18 above, it was confirmed that the fragrance compositions of the present invention provided a fresh and juicy odor.

0.3 part by mass of each fragrance composition of Examples 23 and 24 shown in Table 17 was blended into 99.7 parts by mass of a liquid detergent composition for tableware having the composition shown in Table 19. A suitable amount thereof was allowed to soak into a sponge for washing tableware and then the odor perceived when a dish was washed therewith was evaluated. As a result, a diffusive and fresh citrus odor was perceived and an effect of enhancing a natural grapefruit odor was found. On the other hand, with respect to the fragrance composition of Comparative Example 15, the odor perceived when a dish was washed in the same manner was evaluated. As a result, freshness obtained in the cases where the fragrance compositions of Examples 23 and 24 were used was not perceived.

TABLE 19

| Ingredients | % by mass |
|---|---|
| Sodium polyoxyethylene alkyl ether sulfate | 30 |
| N-Lauryl-N,N-dimethylamine oxide | 6 |
| Alkyl glucoside | 5 |
| Sulfobetaine | 2 |
| Ethanol | 2.5 |
| Propylene glycol | 4 |
| p-Toluenesulfonic acid | 3 |
| Magnesium chloride-hexahydrate | 3.3 |
| Water | Balance |
| Total | 99.7 |

0.05 part by mass of the fragrance composition of Example 24 shown in Table 17 was blended into 99.95 parts by mass of a liquid aromatic deodorant composition having the composition shown in Table 20. As a result, a fresh citrus odor was perceived by the sensory evaluation that was carried out at the mouth of the bottle. It was sprayed five times over the whole surface of a 30-cm square cotton cloth uniformly using a commercially available manual spray container. As a result, a diffusive and fresh citrus odor was perceived.

TABLE 20

| Ingredients | % by mass |
|---|---|
| Cyclodextrin | 1 |
| Green tea extract | 0.5 |
| Ethanol | 5 |
| Water | Balance |
| Total | 99.95 |

Examples 25 to 26 and Comparative Example 16

Fragrance Compositions for Body Cleaners

Compound (I) obtained in Production Example 2 and Compound (II) obtained in Production Example 3 were used to prepare citrus-floral-type fragrance compositions for body cleaners, each of which had the composition shown in Table 21. Odor evaluation was carried out by the same method as in Example 1 and the odor perceived when each of them was used for a body cleaner was assessed by sensory evaluation. The results of the sensory evaluation are shown in Table 22.

TABLE 21

|  | C. Example | Examples | |
|---|---|---|---|
|  | 16 | 25 | 26 |
| Methyl dihydrojasmonate | 220 | 220 | 220 |
| Galaxolide[15] | 100 | 100 | 100 |
| Acetyl cedrene | 100 | 100 | 100 |
| Lemon oil | 80 | 80 | 80 |
| Lime oil | 70 | 70 | 70 |
| Dihydromyrcenol | 60 | 60 | 60 |
| Helional | 50 | 50 | 50 |
| Ambrettolide | 50 | 50 | 50 |
| Orange oil | 30 | 30 | 30 |
| Citronellol | 20 | 20 | 20 |
| Cinnamic alcohol | 15 | 15 | 15 |
| Nutmeg oil | 6 | 6 | 6 |
| Citral | 5 | 5 | 5 |
| Calone[16] | 5 | 5 | 5 |
| Muscone | 5 | 5 | 5 |
| Ambroxan | 5 | 5 | 5 |
| δ-Damascone | 2 | 2 | 2 |
| n-Decanal | 1 | 1 | 1 |
| n-Octanal | 1 | 1 | 1 |
| Compound (I) | — | 144 | 120 |
| Compound (II) | — | 6 | 30 |
| Dipropylene glycol | 175 | 25 | 25 |
| Total | 1000 | 1000 | 1000 |

[15]Galaxolide: IFF (Trade Name), Compound Name: 1,3,4,6,7,8-Hexahydro-4,6,6,7,8,8-hexamethylcyclopenta-γ-2-benzopyran
[16]Calone: Firmenich (Trade Name), Compound Name: 7-methyl-3,5-dihydro-2H-benzo-dioxepin-3-one

TABLE 22

| C. Example 16 | A citrus-floral odor |
|---|---|
| Example 25 | Floral softness was further added and a musk odor was enhanced, which made the fragrance voluminous. |
| Example 26 | Floral softness was further added and a musk odor was enhanced, which made the fragrance voluminous. |

As shown in Table 22, it was confirmed that the fragrance compositions of the present invention had floral softness further added thereto and a musk odor was enhanced, which made the fragrance voluminous.

1 part by mass of the fragrance composition of Example 23 shown in Table 17 was blended into 99 parts by mass of a body cleaner composition having the composition shown in Table 23 and the odor thereof was evaluated at the mouth of the bottle. As a result, a floral soft odor with sweetness of citrus was perceived.

TABLE 23

| Components (% by mass) |  |
|---|---|
| Palm fatty acid | 30.0 |
| Potassium lauroyl polyoxyethylene (EO = 2.0) sulfate | 5.0 |
| Carboxymethyl cellulose | 0.5 |
| Potassium hydroxide | 7.0 |
| Water | Balance |
| Total | 99 |

Examples 27 and 28 and Comparative Example 17

Fragrance Compositions for Hair Cleaners

Compound (I) obtained in Production Example 2 and Compound (II) obtained in Production Example 3 were used to prepare green-floral-type fragrance compositions for hair cleaners, each of which had the composition shown in Table 24. Odor evaluation was carried out by the same method as in Example 1 and the odor perceived when each of them was used for a hair cleaner was assessed by sensory evaluation. The results of the sensory evaluation are shown in Table 25.

TABLE 24

|  | C. Example | Examples | |
|---|---|---|---|
|  | 17 | 27 | 28 |
| Methyl dihydrojasmonate | 250 | 250 | 250 |
| Phenyl hexanol | 100 | 100 | 100 |
| Ethyllinalool | 100 | 100 | 100 |
| Phenylethyl alcohol | 80 | 80 | 80 |
| Hexyl cinnamaldehyde | 50 | 50 | 50 |
| Citronellol | 50 | 50 | 50 |
| Amber Core | 50 | 50 | 50 |
| Phlorol | 50 | 50 | 50 |
| Pentalide | 50 | 50 | 50 |
| Dimethyl benzyl carbinol | 40 | 40 | 40 |
| Dimethylbenzylcarbinyl acetate | 40 | 40 | 40 |
| Terpineol | 20 | 20 | 20 |
| Triplal | 10 | 10 | 10 |
| cis-3-Hexenol | 5 | 5 | 5 |
| Citronellyl nitrile | 5 | 5 | 5 |
| Compound (I) | — | 96 | 80 |
| Compound (II) | — | 4 | 20 |
| Dipropylene glycol | 100 | — | — |
| Total | 1000 | 1000 | 1000 |

TABLE 25

| C. Example 16 | A green-floral odor with a strong grassy green odor, without softness |
|---|---|
| Example 25 | Floral softness was added and harmonized with a green feeling, which resulted in a natural refreshing odor. |
| Example 26 | Floral softness was added and harmonized with a green feeling, which resulted in a natural refreshing odor. |

As shown in Table 25 above, it was confirmed that the fragrance compositions of the present invention provided floral softness that harmonized with a green feeling, which resulted in a natural refreshing odor.

0.5 part by mass of the fragrance composition of Example 27 shown in Table 24 was blended into 99.5 parts by mass of a hair cleaner composition having the composition shown in Table 26, and the odor thereof was evaluated at the mouth of the bottle. As a result, a natural green-floral odor with refreshingness was perceived.

TABLE 26

| Components (% by mass) | |
|---|---|
| Sodium polyoxyethylene lauryl ether sulfate (30% Aqueous solution) | 55 |
| Lauric acid diethanolamide | 11 |
| Purified water | Balance |
| Total | 99.5 |

INDUSTRIAL APPLICABILITY

Since the fragrance compositions of the present invention contain 3,6-dimethylheptane-2-ol (Compound (I)), they can be used as fragrance materials having a strong floral fragrance note and each of them can be used alone or in combination with another component, as a fragrance component of a toiletry product such as a hair cosmetic and a softener.

The invention claimed is:

1. A fragrance composition, comprising 3,6-dimethylheptane-2-ol and 7-methyloctane-3-ol.

2. The fragrance composition according to claim 1, wherein said 3,6-dimethylheptane-2-ol and said 7-methyloctane-3-ol are present in said fragrance composition in a mass ratio of 70/30 to 99.9/0.1 (3,6-dimethylheptane-2-ol/7-methyloctane-3-ol).

3. The fragrance composition according to claim 1, wherein said 3,6-dimethylheptane-2-ol and said 7-methyloctane-3-ol are are present in said fragrance composition in a mass ratio of 80/20 to 99/1 (3,6-dimethylheptane-2-ol/7-methyloctane-3-ol).

4. The fragrance composition according to claim 1, wherein said 3,6-dimethylheptane-2-ol and said 7-methyloctane-3-ol are present in said fragrance composition in a mass ratio of 90/10 to 95/5 (3,6-dimethylheptane-2-ol/7-methyloctane-3-ol).

5. The fragrance composition according to claim 1, further comprising at least one member selected from the group consisting of an alcohol other than 3,6-dimethylheptane-2-ol and 7-methyloctane-3-ol; an ester; a carbonate; an aldehyde; a ketone; an ether; and a lactone.

6. The fragrance composition according to claim 5, wherein said alcohol other than 3,6-dimethylheptane-2-ol and 7-methyloctane-3-ol is at least one alcohol selected from the group consisting of a terpene alcohol and an aliphatic alcohol.

7. The fragrance composition according to claim 5, wherein said ester is at least one ester selected from the group consisting of acetate ester, propionate ester, salicylate ester, jasmonate ester, methyl atrarate, ethyl tricyclo[5.2.1.0] decan-2 carboxylate, and ethyl 2-cyclohexyl propionate.

8. The fragrance composition according to claim 5, wherein said aldehyde is at least one aldehyde selected from the group consisting of 2,4-dimethyl-3-cyclohexene-1-carboxaldehyde, 3-(4-tert-butylphenyl)propanal, p-tert-butyl-α-methylhydrocinnamaldehyde, 3-(o-(and p-)ethylphenyl)-2,2-dimethylpropionaldehyde, α-hexyl cinnamaldehyde, and alpha-methyl-1,3-benzodioxole-5-propanal.

9. The fragrance composition according to claim 5, wherein said ether is at least one ether selected from the group consisting of rose oxide, ambroxan, galaxolide, and phenylacetaldehyde dimethyl acetal.

10. The fragrance composition according to claim 1, further comprising an oil.

11. The fragrance composition according to claim 1, further comprising a surfactant.

12. A method of imparting a fragrance to a fabric treatment composition, comprising adding a fragrance composition according to claim 1 to said fabric treatment composition.

13. A method of imparting a fragrance to a softener, comprising adding a fragrance composition according to claim 1 to said softener.

14. A method of imparting a fragrance to a cosmetic, comprising adding a fragrance composition according to claim 1 to said cosmetic.

15. A method of imparting a fragrance to a hair cosmetic, comprising adding a fragrance composition according to claim 1 to said hair cosmetic.

16. A method of imparting a fragrance to a body cosmetic, comprising adding a fragrance composition according to claim 1 to said body cosmetic.

17. A method of imparting a fragrance to a perfume, comprising adding a fragrance composition according to claim 1 to said perfume.

* * * * *